US005747346A

United States Patent [19]
Pullarkat et al.

[11] Patent Number: 5,747,346
[45] Date of Patent: May 5, 1998

[54] DETECTION OF NOVEL CARBOHYDRATES DIRECTLY ASSOCIATED WITH CHRONIC ALCOHOLISM

[75] Inventors: Raju K. Pullarkat; Premila S. Pullarkat; Simhachalam Raguthu, all of Staten Island, N.Y.

[73] Assignee: Research Foundation for Mental Hygiene, Inc., Albany, N.Y.

[21] Appl. No.: 259,730

[22] Filed: May 27, 1994

Related U.S. Application Data

[63] Continuation-in-part of Ser. No. 751,539, Aug. 29, 1991, abandoned.

[51] Int. Cl.$^6$ .......................... G01N 33/00; G01N 30/90; G01N 30/02; G01N 21/77
[52] U.S. Cl. .................... 436/94; 436/93; 436/127; 436/129; 436/131; 436/161; 436/162; 436/169; 422/56; 422/61
[58] Field of Search ............................. 436/94, 161, 162, 436/169, 93, 127, 129, 131, 132; 422/56-58, 61

[56] References Cited

U.S. PATENT DOCUMENTS

| | | | |
|---|---|---|---|
| 2,524,414 | 10/1950 | Wolfrom | 436/94 X |
| 2,845,439 | 7/1958 | Reiners . | |
| 4,246,347 | 1/1981 | Neidleman et al. | 435/105 |
| 4,463,098 | 7/1984 | Hoberman | 436/67 |
| 4,514,563 | 4/1985 | Fujiyama et al. | 435/101 X |
| 4,575,551 | 3/1986 | Fujiyama et al. | 435/101 X |
| 4,770,996 | 9/1988 | Tabakoff | 435/18 |
| 4,837,144 | 6/1989 | Sugiyama | 436/94 X |

FOREIGN PATENT DOCUMENTS

| | | | |
|---|---|---|---|
| 1355933 | 11/1987 | U.S.S.R. | 436/94 |

OTHER PUBLICATIONS

I. Smith "Chromatographic Techniques" Interscience Publishers, Inc.: New York, 1958, pp. 164–177.
R.T. Williams "Detoxication Mechanisms" John Wiley & Sons Inc.: New York, 1959, pp. 46–55.
J. Kocourek et al. *J. Chromatog.* 1966, 24, 117–124.
T. Mizuno et al. *Shizuoka Daigaku Nogakubu Kenyu Hokoku* 1971, 29–37.
T. Kartnig et al. *J. Chromatog.* 1971, 61, 375–377.
T. Kartnig et al. *Plant. Med.* 1972, 21, 144–149.
H.A.G. Müller et al. *Clin. Chim. Acta* 1977, 78, 17–21.
N. Iizima et al. *J. Chromatog.* 1980, 193, 464–469.
T. Kawada et al. *Agric. Biol. Chem.* 1985, 49, 441–448.
E. Mentasti et al. *J. Chromatog.* 1985, 322, 177–189.
F. Caccamo et al. *J. Chromatog.* 1986, 362, 47–53.
J. G. Streeter *Plant. Phsyiol.* 1987, 85, 768–773.
B. Y Lee et al. *LC-GC* 1992, 10, 884–887.
K. Kawahara et al. *Biochem. Biophys. Acta* 1982, 712, 571–575.
R.K. Pallarkat et al. *Alcohol. Clin. Exp. Res.* 1985, 9, 28–30.
J.M Bobbitt "Thin Layer Chromatography" 1963, Reinhold Publishing Corporation: New York, 61–63.

H. Stibler et al. *Alcohol. Clin. Exp. Res.* 1986, 10, 61–64.
J. Iwamura et al. *Chem. Abstr.* 1986, 105, 108686d.
Y. Israel et al. *Proc. Natl. Acad. Sci.* 1986, 83, 7923–7927.
B.K. Tang et al. *Biochem. Biophys. Res. Commun.* 1986, 140, 924–927.
I.A. Kamil, et al. *Biochem. J.* 1953, 53, 129–136.
I.A. Kamil et al. *Biochem. J.* 1953, 53, 390–392.
H.R. Bollinger et al. "Thin–Layer Chromatography A Laboratory Handbook".
E. Stahl ed. 1965, Springer Verlag: New York, 14–25, 466–469 and 483–501.
T. Kozu *Chem. Abstr.* 1975, 83, 126992g.
Z. Zilic *J. Chromatog.* 1979, 164, 91–94.
D.M. Chambers et al. *Gut* 1981, 22,992–996.
K.O. Lewis et al. *Brit. Med. J.* 1981, 283, 1531–1532.
E.L. Storey et al. *Lancet* 1987, 1292–1293.
A Sieg et al. *Gastroenterology* 1987, 93, 261–265.
R.P. Risto et al. *Alcohol. Clin. Exp. Res.* 1987, 11, 525–527.
B. Tabakoff et al. *Ne Eng. J. Med.* 1988, 318, 134–139.
R. Klaus et al. *Methods Enzym.* 1988, 160, 159–175.
H. Stibler et al. *Alcohol.* 1988, 5, 393–398.
S.S. Narayan et al. *Xenobiotica* 1991, 21, 515–524.
B.Y. Lee et al. *Chem. Abstr.* 193, 118, 187131P.
T. Kozu, 1973, "Gas Chromatographic Analysis of Ethyl–β–D–Glucuronide in Human Urine", Shinshu Igaku Kasahi, Shinsu Medical Journal, 21 (5)(6), 595–601.
P.I. Jaakonmaki et al., 1967, "The Characterization by Gas–Liquid Chromatography of Ethyl β–D–Glucosiduronic Acid as a Metabolite of Ethanol in Rat and Man", *Eur. J. Pharamacol.*, 1:63–70.
J.E. Manautou and G.P. Carlson, 1992, "Comparison of Pulmonary and Hepatic Glucuronidation and Sulphation of Ethanol in Rat and Rabbit in vitro", *Xenobiotica*, 22(11):1309–1319.
I.A. Kamil et al., 1952, "A New Aspect as Ethanol Metabolism: Isolation of Ethyl Glucuronide," *Biochem. J.*, 51:22–23.

*Primary Examiner*—Arlen Soderquist
*Attorney, Agent, or Firm*—Morgan & Finnegan, L.L.P.

[57] ABSTRACT

Chronic or long-term alcohol consumption is detected and monitored by determining the level of a newly-observed, alcohol-specific carbohydrate in body fluids (e.g. urine) of subjects by calorimetric reaction using qualitative and quantitative assay methods. The alcohol-specific carbohydrate have been identified as a novel ethyl glucuronide. Ethyl glucuronide is observed and detected in direct response to alcohol consumption in body fluids, and can be isolated and purified. Simple, economical, and reproducible assay methods, such as a spot assay and an ascending or thin layer chromatography assay, provide reliable, objective, and sensitive methods for detecting and monitoring a chronic alcoholic condition. Both the presence of the alcohol-specific ethyl glucuronide and a substantial increase in its levels are indicative of chronic alcoholism. Since the novel ethyl glucuronide is produced and appears as a direct response to chronic alcohol intake, the novel carbohydrate is considered to be a unique biomarker for the detection of alcoholism, with virtually no possibility of false positive results.

71 Claims, 12 Drawing Sheets

1  2  3  4  5  6  7

1  2  3  4  5  6  7

1  2  3  4  5  6  7  8

1  2  3  4  5  6  7  8

1  2  3  4  5

1   2   3   1   2   3

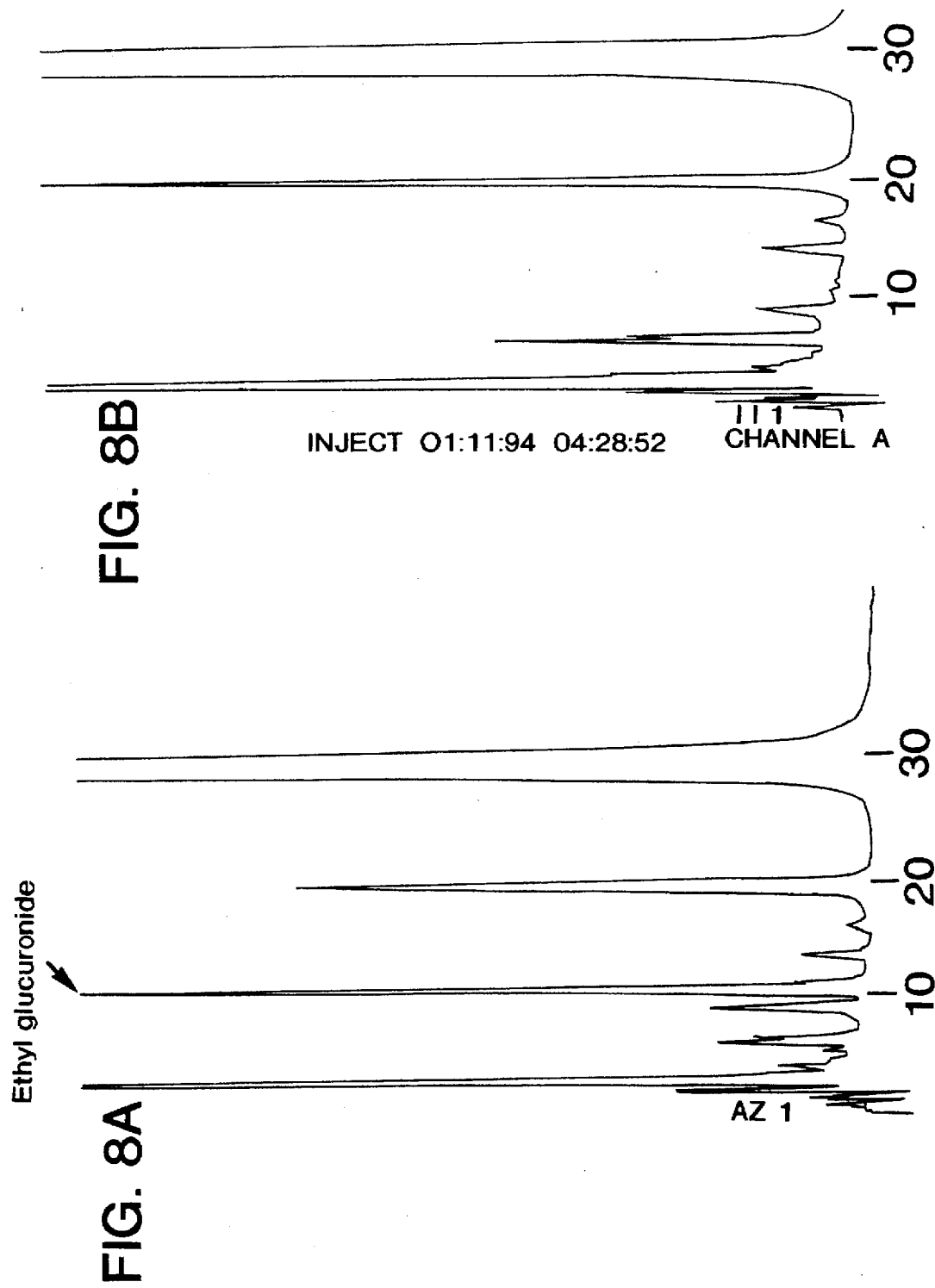

NMR Spectrum

DETECTION OF NOVEL CARBOHYDRATES DIRECTLY ASSOCIATED WITH CHRONIC ALCOHOLISM

This is a continuation-in-part of U.S. application Ser. No. 07/751,539 application filed on Aug. 29, 1991, now abandoned.

FIELD OF THE INVENTION

The present invention describes the isolation and characterization of a novel carbohydrate biomarker of alcohol consumption and relates generally to improvements in detecting and monitoring chronic alcoholism.

BACKGROUND OF THE INVENTION

Alcoholism is a major health and economic problem which imposes broad reaching concerns not only to the afflicted individuals, but to society at large. In the United States alone, at least ten to twenty million people are classified as chronic alcoholics and long-term alcohol abusers. In addition, other countries have serious problems with chronic alcohol consumption as well as with the objective diagnosis and detection of long-term alcohol use.

For example, in the United States, health and medical costs related to alcohol abuse are continually increasing and are estimated to be on the order of 31.6 billion dollars annually. In 1980, lost employment and reduced productivity due to costs related to alcohol abuse were estimated to be approximately 54.7 billion dollars. In 1983, this figure jumped to 116.9 billion dollars, 60% of which was attributed to lost employment and reduced productivity, and 13% of which was attributed to health care costs. Furthermore, at least 1.5 million Americans participate in alcohol rehabilitation programs and another 0.5 million chronic alcoholics are in contact with medical and treatment professionals. Thus, at least 2 million people, at a minimum, could conceivably use the test methods of the present invention several times during the course of rehabilitation.

It is known that chronic (i.e. over a period of weeks, months, or longer) alcoholic and long-term alcohol users rarely admit their excessive consumption of alcohol. In spite of attempts to standardize the diagnosis of alcohol abuse and chronic alcoholism based on operational and functional criteria, many problems exist in the detection and diagnosis of alcohol-related disorders. One major problem is that patient cooperation is required, and often, alcoholics do not approach their physicians to ask for help specifically to stop their excessive or pathological drinking. Unfortunately, even when questioned directly by their physicians, alcoholics rarely disclose the true extent of their alcohol consumption, and often deny and minimize any association between their use of alcohol and their other symptoms or problems. Because it is difficult to detect and diagnose alcoholism and alcohol abuse in patients, physicians frequently misdiagnose or underdiagnose alcohol-related disorders.

As evidenced by the foregoing explanantion, there is a real need for simple and reliable tests which could help physicians in their desire and ability to detect alcoholism and monitor alcohol abuse. An early diagnosis of chronic alcohol abuse would also allow constructive intervention therapy at a stage when predicted recovery from alcoholism would be more favorable. Moreover, improvements in the ability to monitor the extent of abstinence in treated alcoholics would permit researchers to better assess the efficacy of various treatment regimens for chronic alcoholism.

Thus, biological and/or biochemical markers which serve as objective, physiological measures of alcohol consumption are extremely important for patient clinical care and research when a valid drinking history is required. In addition, reliable, reproducible, and economical methods of detecting and monitoring these biomarkers are needed. Such biological markers and detection methods would provide treatment professionals and researchers with an unbiased and credible tool for monitoring patient compliance with treatment goals. In addition, there is a need for objective and dependable biomarkers of alcohol consumption to aid in the diagnosis and treatment of conditions other than alcoholism when alcohol consumption is suspected.

Until the present invention, a simple, reliable, and objective biomarker of chronic alcohol consumption and the methods of detecting and monitoring the presence of such a biomarker in test individuals has been rather limited in scope and has frequently lacked sensitivity and ease of detection and use. An ideal biomarker for chronic alcohol consumption would be a direct derivative of alcohol that responds to and appears only after continued chronic intake of alcohol. Until the present invention, such a novel biomarker which is a direct product of heavy alcohol consumption had not been discovered or previously described.

DISCUSSION OF THE ART

Many current biological indicators of alcohol consumption are severely hampered by the fact that alcohol is fully and quickly eliminated from the body through oxidative metabolism. Thus, the measurement of alcohol in and of itself as a biomarker either in breath or in body fluids indicates only the very recent consumption of alcohol. Because of the rapid rate of oxidative metabolism, the direct detection of alcohol per se in breath or body fluids can be assessed only within a few hours of a drinking episode. Thus, the direct measurement of alcohol in a subject will often fail to detect drinking or alcohol consumption, even in an individual who has consumed alcohol over an extended period of time, but who has abstained during the most recent 24 hour period.

Unlike the present invention, a number of enzyme and blood chemistry assays, which are available in the clinical laboratory and have been used to detect heavy alcohol consumption, are not readily adaptable for routine, accurate, rapid, and cost-effective diagnostic testing. Previously reported assays also suffer from loss or degradation of the product being monitored over a short time period. Representative examples include gamma-glutamyltranspeptidase (GGT) (Rosalki, S.B. and Rau, D. (1972). *Clinica Chemica Acta*, 39:41; Rollason, J.G. et al. (1972). *Clinica Chemica Acta*, 39:75); aspartate aminotransferase (AST) (Bernadt, M.W., (1982). *Lancet*, 1:325); alanine aminotransferase (ALT); glutamate dehydrogenase (GDH) (Schellenberg, F., (1983). *Ann. Biol. Clin.*, 41:255); mean corpuscular volume (MCV) (Whitfield et al. (1978). *Ann. Clin. Biochem.:* 15, 297–303); and alpha-amino-n-butyric acid/leucine ratio (AANB/L). Several of these assays are sometimes combined to increase the discriminating power of each test separately; however, the applicability of these biochemical parameters to routine clinical use is limited by the lack of overall specificity, sensitivity, and reliability of the tests. GGT, one of the most commonly relied upon biochemical measures of heavy alcohol use, is elevated in patients with liver disease of both non-alcoholic and alcoholic origin. Furthermore, increased levels of GGT can be found not only as a consequence of obesity, pancreatic disease, diabetes, hyperlipidemia, heart disease, smoking and trauma, but also as a consequence of the use of drugs which induce microsomal enzymes, particularly anti-epileptic and anti-coagulant drugs. The AANB/L ratio also appears to be influenced by alcoholic and non-alcoholic liver disease. Moreover, the requirement of an amino acid analyzer to perform the assays makes many of these tests expensive and less conducive to routine screening and diagnostic procedures.

Other methods for the biochemical diagnosis of chronic alcoholism suffer from practical limitations and inefficient features. For example, urinary dolichol levels have been suggested to be a biomarker for chronic alcoholism (Pullarkat, R. K. and Raguthu, S., (1985). *Alcohol. Clin. Exp. Res.* 9: 229–231). This finding has been confirmed by other laboratories (Roine, R. P. et al., (1987). *Alcohol. Clin. Exp. Res.* 11: 525–527; Salaspuro, M. P., et al., (1987). In: Genetics and Alcoholism, Ed. Alan R. Liss, Inc., 231–240; Roine, R. P., (1988). *Alcohol* 5: 229–231). Estimation of the extremely small levels of urinary dolichol that are able to be detected requires the use of sophisticated equipment such as high performance liquid chromatography (HPLC). Thus, dolichol is not easily adaptable for rapid and facile clinical evaluation and testing. Furthermore, the appearance of dolichol, like other known markers of alcohol consumption, results from secondary effects of alcohol on metabolism. Since dolichol is present only in small amounts (e.g. nanograms/milliliter) in the urine of chronic alcoholics, it is difficult to detect and assess accurately without using large amounts of starting sample, elaborate sample preparation techniques, and expensive clinical research instruments.

Measurement of acetaldehyde-protein adducts in urine or other body fluids by HPLC or in body fluids and cells by an immunoassay method has been reported as methods for detecting chronic alcoholism (Tang, B. K. et al., (1986). *Biochem. Biophys. Res. Comm.* 140: 924–927; Israel, Y. et al., (1986). *Proc. Natl. Acad. Sci.* 83: 79237927; U.S. Pat. No. 4,900,664 to Y. Israel and R. Amon, filed Oct. 2, 1986). However, although these adducts are not secondary biproducts of alcohol, they are known to be very unstable and to decompose completely after 24 hours. The HPLC method also requires the use of sophisticated equipment which is cumbersome and not easily adaptable for routine, clinical testing.

The reduction of monoamine oxidase in platelets of chronic alcoholics has been demonstrated (Tabakoffetal., (1988). *New Engl. J. Med.* 318: 134–149). However, the changes observed are marginal and the detection procedures are very time-consuming to perform, since platelet membranes must be prepared and various enzyme assays must be conducted.

Carbohydrate deficient-species of transferrin in serum has been demonstrated to be a specific marker for chronic alcohol consumption (Stibler, H. et al., (1986). *Alcohol. Clin. Exp. Res.* 10 (5):535–544; Behrens, U. J. et al., (1988). *Alcohol. Clin. Exp. Res.* 12 (3):427–432; Storey, E. L. et al., (1987). *Lancet* 1: 1292). The methods used involve an isocratic anion exchange chromatography of isotransferrins followed by a double antibody transferrin radioimmune assay. These procedures are quite laborious to perform and cannot always be readily adapted as rapid clinical tests.

Commonly-occurring sugars in biological fluids have been separated and quantified by a one-dimensional thin layer chromatography (TLC) method (Zilik, Z. et al., (1979). *J. Chromatog.* 164:91–94). This method uses a reagent comprised of diphenylamine, aniline, and phosphoric acid to detect the normally low levels of known sugars commonly-found in human urine and plasma, as well as to detect glucose present in the urine of diabetics. Zilic et al. do not contemplate either the detection of chronic alcoholism or the presence of a novel biomarker linked directly to chronic alcohol consumption.

SUMMARY OF THE INVENTION

The invention provides rapid, reliable, and objective testing and assay methods to detect and measure the levels of a newly-discovered carbohydrate biochemical marker found to be associated with long-term, chronic alcohol intake. The new biomarker is a novel derivative of alcohol, not previously observed or known to be directly linked to excessive alcohol consumption. Specifically, the biomarker detected in the described assays is a novel ethanol glycoconjugate (also called simply "glycoconjugate") which is produced as a direct response to alcohol intake. The ethanol glycoconjugate is identified as ethyl glucuronide, which, in general terms, is an alcohol (i.e., ethanol) conjugated to glucuronic acid.

Purification and isolation of the alcohol-associated ethanol glycoconjugate from urine samples demonstrated that it produced a single spot on thin layer chromatographs. Following acid hydrolysis of the ethanol glycoconjugate, ethyl glucuronic acid was produced as the major component (greater than 90% of the glycoconjugate) and glucuronic acid lactone was produced as a minor species or reaction product of the acid hydrolysis. The ethyl glucuronide, more particularly ethyl β-glucuronide, is called ethyl glucuronic acid in its acid form and is a novel biomarker for alcoholism as detected by the assay methods described herein. It is to be understood that the detection of the novel ethanol glycoconjugate is identical to the detection of ethyl glucuronide in samples, since the newly-discovered, alcohol-specific glycoconjugate is ethyl glucuronide.

Accordingly, the invention provides several assay methods for reproducibly detecting the alcohol-specific glycoconjugate in a test sample (e.g. urine or other body fluids or tissue sample preparations) by means of a colorimetric reaction between a diphenylamine/aniline/phosphoric acid (DAP) reagent and the glycoconjugate, which is directly associated with chronic alcohol consumption. The invention further embodies a simple assay method, particularly a spot test, and a simple chromatography assay method to identify individuals who are chronic alcoholics or long-term alcohol consumers. A rapid, reproducible calorimetric assay method provides a qualitative test for chronic alcohol consumption. A rapid, reproducible ascending chromatography method (e.g. thin layer chromatography) in an appropriate solvent mixture provides both a qualitative and quantitative test for identifying and measuring the novel glycoconjugate associated with chronic alcohol consumption.

The present invention allows objective and inexpensive assays for chronic alcoholism based on the detection and measurement of the ethanol glycoconjugate present in body fluids (e.g. urine) of long-term alcohol users, and thus alleviates the need to rely solely on subjective and personally interpretive data and input from the individuals being tested. The invention is useful for the determination of chronic alcohol consumption by humans and animals. In addition, the biochemical marker and methods of this invention have a profound impact on the detection and potential prevention of fetal alcohol syndrome and fetal alcohol effects leading to mental retardation and other severe physical defects, since pregnant women can be tested and monitored in an efficient, non-invasive, and non-traumatic manner.

The subject invention is based on the discovery that chronic alcoholism can be determined and monitored by simple, objective test procedures via the detection of a novel, alcohol-specific ethanol glycoconjugate present in the urine or other body fluids of long-term alcohol consumers, but not present at any detectable level in the urine of non-alcoholics, progressively recovering alcoholics, occasional drinkers, or social drinkers. In addition, the alcohol-specific biomarker disclosed herein is not related to or affected by specific disease states that potentially complicate other types of analyses for alcohol use and/or abuse.

The present invention improves on the capability to diagnose, detect, and monitor chronic alcoholism in an objective fashion, using fast and reliable methods to assay for the distinct, atypical glycoconjugate biomarker which serves to signal that an individual has indulged in excessive, chronic alcohol consumption.

The invention also provides stable, biological markers and generally-applicable methods for the objective detection of long-term alcohol consumption in subjects regardless of age, race, or gender.

The invention further provides an newly-detected ethyl glucuronide which can be isolated and purified for use in generating specific antibodies of various types, and in diagnosing and assaying for alcoholism in a variety of ways known to those having skill in the art.

DESCRIPTION OF THE DRAWINGS

FIG. 1A is an actual photograph of the TLC; FIG. 1B is a replica of the chromatograph as it appears in the FIG. 1A photograph.

FIG. 2A is an actual photograph of the TLC; FIG. 2B is a replica of the chromatograph as it appears in the FIG. 2A photograph.

FIG. 3A is an actual photograph of the spot assay; FIG. 3B is a replica of the spot assay as it appears in the FIG. 3A photograph.

FIG. 4A is an actual photograph of the chromatograph; FIG. 4B is a replica of the chromatograph as it appears in the FIG. 4A photograph.

FIG. 5A is an actual photograph of the chromatograph; FIG. 5B is a replica of the chromatograph as it appears in the FIG. 5A photograph.

FIGS. 7A and 7B are as follows: Lane 1: isolated alcohol-specific glycoconjugate; lane 2: dolichol; lane 3: chemically-synthesized 1-O-ethyl glucuronide. FIG. 7A is reacted with DAP reagent following thin layer chromatography. FIG. 7B is charred after spraying with potassium dichromate in sulfuric acid. After charring to allow visualization of carbon, dolichol, which does not react with the DAP reagent, is seen as the spot migrating at the very top of the TLC in lane 2 of FIG. 7B.

FIGS. 8A and 8B show HPLC analyses of the phenacyl ester derivatives isolated from urine samples. FIG. 8A is the HPLC spectrum of the phenacyl ester derivative from urine of rats fed a diet containing 36% of the calories from alcohol. FIG. 8B is the HPLC spectrum of the phenacyl ester derivative from urine of pair-fed control rats which received no dietary alcohol. Ethyl glucuronide phenacyl ester had a retention time of 10.8 minutes. A discrete peak identified as ethyl glucuronide phenacyl ester is clearly observed in the alcohol-fed rat urine sample, but is completely absent in the control sample with no alcohol consumption. Since 0.25 µl of starting sample was used to see the striking result, both the sensitivity and the specificity of the assay are demonstrated.

DETAILED DESCRIPTION OF THE EMBODIMENTS

Figure 1A:
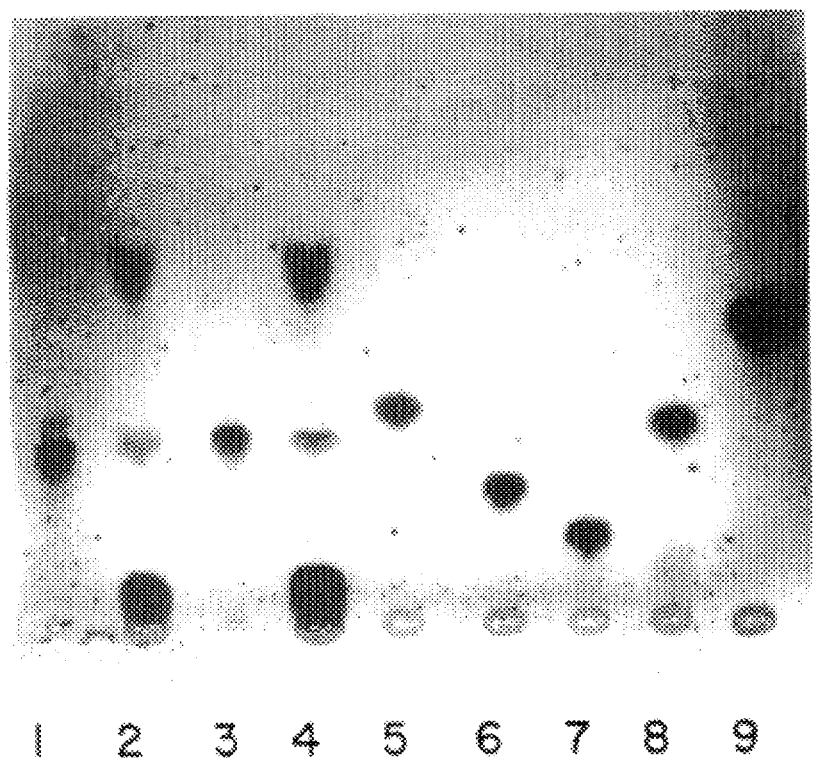
FIGS. 1A and 1B show a thin layer chromatograph (TLC), first run (i.e. developed) in a solvent mixture comprised of chloroform/methanol/acetic acid/water in the proportions of 50:20:6:1.5, by volume, and then reacted with diphenylamine/aniline/phosphoric acid (DAP) reagent. Lane 1 shows the migration of the alcohol-specific ethyl glucuronide detected in a urine sample from a chronic alcoholic. Lane 2 shows that acid-hydrolysis of the ethyl glucuronide from the same urine sample as shown in Lane 1 resolves this glycoconjugate into three DAP-reactive carbohydrate components in this particular solvent mixture. Lane 3 shows another, independent urine sample from a chronic alcoholic and Lane 4 shows that acid-hydrolysis of the alcohol-specific ethyl glucuronide in the sample from Lane 3 resolves this glycoconjugate into three DAP-reactive components in this solvent mixture. Lanes 5–9 show the following standard monosaccharides run as controls: Lane 5: glucose; Lane 6: sucrose; Lane 7: lactose; Lane 8: galactose; Lane 9: xylose. For all samples shown in FIGS. 1A and 1B, the mobility (in cm) and $R_f$ values correspond with the values shown in TABLE 1 herein. An $R_f$ value is a constant ratio defined as the distance in centimeters (cm) in which a material in solution moves as a function of the distance in centimeters in which the solvent moves. Shown in FIGS. 1A and 1B are the direction of sample migration away from the origin. The TLC provides qualitative results concerning the glycoconjugate.

Newly-found, Alcohol-specific Glycoconjugate Serves as a Biomarker of Chronic Alcohol Consumption The present invention embodies reliable, efficient, qualitative, quantitative, and objective methods for detecting and monitoring chronic alcoholism based on the levels of a newly-identified, alcohol-specific ethanol glycoconjugate found in microgram quantities in the urine or other body fluids of chronic alcoholics. Suitable body fluids in which to detect the alcohol-associated glycoconjugate include blood, serum, plasma, saliva, amniotic fluid, spinal fluid, or fluid from body tissue preparations, as well as fractions of all of these. Urine is preferred as it provides an abundant, easily-attainable, and non-traumatic source material.

Tissue preparations may require processing and/or extraction using conventional methodologies prior to assay. By the methods described herein, the alcohol-specific ethyl glucuronide of the invention is detected in urine and other body fluids. Ethyl glucuronide can be isolated as described herein.

Also as used herein, the term carbohydrate embraces the term saccharide. Carbohydrate is a general term which is known to include saccharides (also called sugars), either a simple saccharide or a combination of saccharides (e.g. monosaccharide, oligosaccharide, polysaccharide, di- and tri-saccharide). In addition, ethyl glucuronide is the ethanol glycoconjugate excreted in the urine or present in body fluid samples following long-term alcohol intake as described. Upon acid hydrolysis, glucuronic acid (detected as a TLC spot having a low $R_f$ value) and glucuronic acid lactone (detected as a TLC spot having a fast $R_f$ value) are produced.

This invention allows the detection of and means for monitoring the newly-identified alcohol-specific ethanol glycoconjugate. The glycoconjugate is a novel carbohydrate which is linked directly to long-term alcohol consumption and which reacts chemically with an easy-to-prepare DAP reagent (i.e. a solution of diphenylamine, aniline, and phosphoric acid). The glycoconjugate further serves as a non-subjective indicator of chronic alcoholism and can be identified in a rapid, safe, reliable, and economical clinical or laboratory assay. In particular, the novel biomarker is present in readily-detectable and quantifiable amounts (i.e. in the order of micrograms per milliliter) in the urine of chronic alcohol consumers, but is not present in detectable levels in the urine of non-alcoholic individuals or in the urine of infrequent alcohol consumers or social (i.e. not long-term) drinkers. The biochemical and clinical indicator of excessive alcohol consumption as described herein is easily identified by the assay methods described. The assays have both high specificity (very few false positives) and high sensitivity (very few false negatives).

Steady and heavy alcohol consumption over a period of approximately 7 to 10 days, or longer, is usually required before the alcohol-specific glycoconjugate can be detected and monitored. In general, alcohol consumption above about 50 to 60 grams per day is usually considered heavy drinking. Such a definition of chronic alcoholism is recognized by those in the art (Ishigami, M. et al. 1991, "Chronic Alcoholism Impedes the Recovery of Renal Function Following Renal Ischemia", *Alcoholism Clin. Exptl. Res.*, 15:757; and Cadveira et al. 1991, "Multimodality Exploration of Event-Related Potentials in Chronic Alcoholics", *Alcoholism Clin. Exptl. Res.*, 15:607). In view of this, the concern of obtaining false-positives or equivocal results when testing otherwise normal or non-alcoholic individuals is substantially reduced. In addition, the levels of the alcohol-specific glycoconjugate decreases with increasing time of abstinence from alcohol consumption. Hence, the progress of rehabilitation of chronic alcoholics can also be monitored efficiently. To monitor the status of alcoholism accurately, the present procedures are is routinely used to compare the amount of the alcohol-specific ethanol glycoconjugate in samples being tested for chronic alcoholism with a standard amount of the glycoconjugate in control samples from chronic alcoholics, with samples from recovering alcoholics, with samples from social drinkers, or with samples from non-alcohol drinkers. Therefore, the present methods can be used effectively to monitor the alcoholic condition.

In fluid test samples (e.g. urine) obtained from chronic alcoholics, an alcoholspecific carbohydrate, identified as ethyl glucuronide, is readily detected by the methods described herein. This distinct carbohydrate can be further resolved after chemical hydrolysis with acids such as hydrochloric acid, as described herein. The newlydiscovered ethyl glucuronide, which appears specifically after chronic alcohol intake, is categorized as a novel type of alcohol-associated sugar acid, and specifically, as a new type of glucuronic acid, not previously reported. Uronic acids are components of many polysaccharides.

The biochemical characterizations and analyses conducted on ethyl glucuronide isolated from chronic alcoholics and from experimental animals fed a steady diet of alcohol have demonstrated that this alcohol-specific compound is not dolichol and is not related to dolichol (see Example IX). It is also known, based on biochemical and structural characterizations, that the alcohol-specific ethanol glycoconjugate detected after chronic alcohol consumption is not a typical or conventional carbohydrate such as glucose, sucrose, galactose, lactose, and xylose, and the like. In addition, protein is not a part of the alcohol-specific glycoconjugate discovered by the inventors. Since the glycoconjugate is produced in direct response to alcohol in the diet, the excretion of ethyl glucuronide as a detoxification product as discovered by the inventors is an advantageous and unequivocal biomarker for the detection of chronic alcohol consumption.

Structure and Characteristics of the Novel Ethyl Glucuronide

The structure of ethyl β-glucuronide, the novel carbohydrate whose appearance is directly linked to chronic alcohol consumption, is shown:

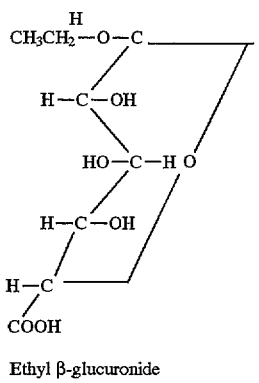

Ethyl β-glucuronide

The chemical nature of the novel ethyl glucuronide was verified by chemical synthesis as described in Example VIII. The chemical structural analysis has more specifically identified this novel glycoconjugate as 1-O-ethyl glucuronide.

This is the first report of a novel ethanol glycoconjugate that is excreted in large amounts in the urine of animals fed with a diet containing ethanol or in the urine of alcoholics. Ethyl glucuronide thus affords an isolatable compound that is uniquely associated with chronic alcohol intake and which is the novel detoxification product of alcohol. The production of ethyl glucuronide as a result of the chemical reaction between ethanol and glucuronic acid provides its direct link to alcohol consumption. In addition, the ethyl glucuronide is not normally produced, and thus is not apparent, in samples of non-alcoholics or non-drinkers, social drinkers, or sporadic drinkers of alcohol (FIGS. 8A and 8B). Consequently, when used as a biomarker for alcoholism, ethyl glucuronide detection eliminates the possibility of false positive results and offers a significant improvement over existing means for detecting and diagnosing alcoholism.

The level of this biomarker in the urine of alcoholics is, on average, in the range of about 10 to 70 µg per mg urinary creatinine, indicating a high degree of sensitivity of detection. The fact that the level of the glycoconjugate remains high for 7 to 14 days after the last alcohol intake indicates that abstenance of alcohol intake for a few days will not fail to detect its presence in chronic alcoholics (see TABLE 4). This feature also provides an improvement over other means for detecting and diagnosing alcoholism.

Figure 11:
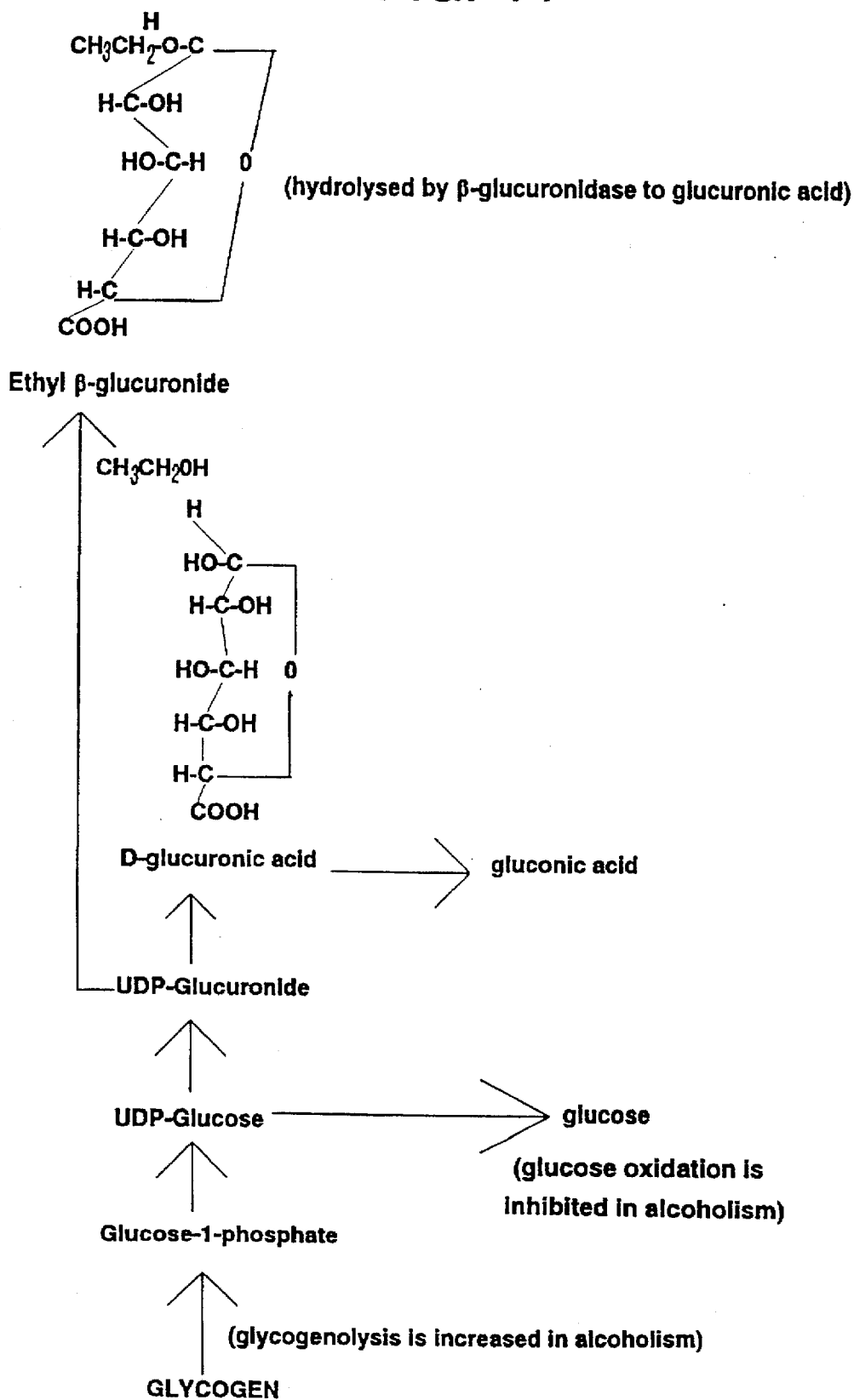
FIG. 11 is a schematic diagram depicting the mode of producing the novel ethyl β-glucuronide detected in chronic alcoholics following alcohol consumption.

Abnormal carbohydrate metabolism in response to ethanol ingestion is a well established phenomenon. For example, ethanol-induced hypoglycemia occurs when glycogen storage is depleted by fasting. However, under well-fed conditions, ethanol consumption does not produce hypoglycemia. On the one hand, ethanol consumption inhibits glucose utilization and gluconeogenesis; while, on the other hand, ethanol stimulates glycogenolysis. The fate of the increased production of glucose-1 phosphate is not clearly understood. Glucose-1-phosphate produced by increased glycogenolysis may result in the increased production of glucose and glucuronic acid. The increased production of glucose may explain why under well-fed conditions, there is no hypoglycemia. One explanation of the presence of the novel ethanol glycoconjugate after chronic alcohol intake is that the increased level of glucuronic acid produced as a result of increased glycogenolysis (which, in turn, is induced by alcohol intake) may react with ethanol to give rise to the novel 1-O-ethyl glucuronic acid, newly detected by the described methods (see FIG. 11).

Isolation and Separation of the Alcohol-specific Glycoconjugate

The alcohol-specific carbohydrate indicative of chronic alcoholism has been characterized and analyzed and has been found to exist in a body fluid sample as an ethanol glycoconjugate or ethyl glucuronide, as described. The characterization analysis of the alcohol-specific ethanol glycoconjugate is a multi-step process and involves isolating the original glycoconjugate from urine samples of chronic alcoholics by preparative, ascending thin layer chromatography (TLC) using a TLC substrate or plate in a water-containing organic solvent mixture. The solvent mixture is preferably either chloroform/methanol/acetic acid/water in the proportions of 50:20:6:1.5, by volume, or chloroform/methanol/water in the proportions of 65:35:5, by volume. The chromatographed glycoconjugate is removed from the TLC plate by manually scraping from the spot, position, or region at which it has migrated on the TLC plate, and then eluting it from the TLC substrate with a suitable organic solvent mixture containing water, such as chloroform/methanol/water in the proportions of 1:1:0.3, by volume, or methanol and water, 50:50, or the like.

The eluted glycoconjugate may be acid-hydrolyzed, preferably in 1 N HCl, at about 80° C. for approximately 15 hours, and the acid-hydrolyzed carbohydrate product(s) are subjected to further TLC chromatography in a solvent mixture suitable for separating individual, acid-hydrolyzed carbohydrate components of the original glycoconjugate. This latter solvent mixture is routinely composed of chloroform/methanol/acetic acid/water in the proportions of 50:20:6:1.5, by volume. In this solvent mixture, the alcohol-specific glycoconjugate migrates at a distance of approximately 3 cm to approximately 5 cm, preferably 4.2 cm to 4.3 cm, from the origin of sample application onto the TLC substrate. The migration values correspond to preferable $R_f$ values of about 0.27 to 0.28 as shown in TABLE 1. In the chloroform/methanol/acetic acid/water solvent mixture, the carbohydrate components which are generated after acid hydrolysis of the ethyl glucuronide migrate after ascending chromatography at three, discrete positions from approximately 1 cm to greater than about 8 cm from the origin of sample application onto the TLC substrate, corresponding to $R_f$ values of about 0.05 to about 0.70, preferably about 0.06 to about 0.53 as related in TABLE 1.

In the acid-hydrolyzed sample described in TABLE 1, the component that moves more slowly than the starting material at the origin of the TLC (i.e. the component represented by the spot whose mobility is 1 cm from the origin as shown in TABLE 1) is glucuronic acid, while the component that moves faster than the starting material at the origin (i.e. the component represented by the spot whose mobility is 8.2 cm from the origin as shown in TABLE 1) is glucuronic acid lactone. The latter component is believed to be formed as a consequence of secondary reactions, such as acid hydrolysis. The minor spot whose mobility is 4.2 cm from the origin as shown in TABLE 1 most likely represents incomplete or non-hydrolyzed material.

After isolation, the ethyl glucuronide may be prepared or formulated in a composition in a suitable solvent, buffer, or excipient. In addition, after elution from the TLC plate with or without further purification as described, the ethanol glycoconjugate may be dried and then resuspended prior to use. If necessary or desired, stabilizers or inhibitors may be added to the composition. Illustrative stabilizers are polyethylene glycol, proteins, other saccharides, amino acids, organic acids, and inorganic acids, which may be used either on their own or in admixtures.

TABLE 1

TLC Solvent System: Chloroform/Methanol/Acetic Acid/Water (50:20:6:1.5, by volume)

| Sample | Mobility from Origin (cm) | $R_f$ Value |
|---|---|---|
| Alcohol-specific carbohydrate #1 | 4.2 | 0.27 |
| Acid-hydrolyzed, alcohol-specific carbohydrate components from #1 (3 components) | 1; 4.2; 8.2 | 0.06; 0.27; 0.53 |
| Alcohol-specific carbohydrate #2 | 4.3 | 0.28 |
| Acid-hydrolyzed, alcohol-specific carbohydrate components from #2 (3 components) | 1; 4.2; 8.2 | 0.06; 0.27; 0.53 |
| Glucose | 4.8 | 0.31 |
| Sucrose | 3.0 | 0.19 |
| Lactose | 2.1 | 0.14 |
| Galactose | 4.3 | 0.28 |
| Xylose | 6.8 | 0.44 |

If the acid-hydrolyzed carbohydrate components are chromatographed in a solvent mixture of chloroform/methanol/water in the proportions of 65:35:5, by volume, two discrete carbohydrate components are resolved, and these alcohol-specific carbohydrates migrate at a distance of greater than 1 cm and greater than 11 cm from the origin of sample application on the chromatography plate, corresponding to $R_f$ values of about 0.07 to about 0.80, preferably about 0.08 to about 0.73, respectively, as shown in TABLE 2. The carbohydrate component which migrates at 1.3 cm in TABLE 2 is glucuronic acid, while the component which migrates at 11.3 cm in this solvent system is glucuronic acid lactone.

TABLE 2

TLC Solvent System: Chloroform/Methanol/Water (65:35:5, by volume)

| Sample | Mobility from Origin (cm) | $R_f$ Value |
|---|---|---|
| Alcohol-specific carbohydrate #1 | 3.7 | 0.24 |
| Acid-hydrolyzed, alcohol-specific carbohydrate components from #1 (2 components) | 1.3; 11.3 | 0.08; 0.73 |
| Glucose | 8.5 | 0.55 |
| Sucrose | 7.0 | 0.45 |
| Lactose | 5.1 | 0.33 |
| Galactose | 8.0 | 0.52 |
| Xylose | 10.2 | 0.66 |

The discrete alcohol-specific ethyl glucuronide can be isolated, purified, and further analyzed for structural identification by using a variety of analytical, chemical, and enzymatic methods known to identify and distinguish among carbohydrate moieties and types, as well as by using mass spectrophotometry, gas chromatography (GC), gas liquid chromatography (GLC), high performance liquid chromatography (HPLC), or nuclear magnetic resonance (NMR) spectroscopy. Several, standard carbohydrates are normally included in the characterization and isolation studies to serve as internal, comparative controls for the analyses. For example, the novel alcohol-specific ethyl glucuronide as detected was analyzed by mass spectroscopy and NMR as disclosed in Example VII, FIGS. 9A and 9B, and FIG. 10.

The results of chromatography in different, suitable solvent mixtures and of acid-hydrolysis analyses have shown that the alcohol-specific carbohydrate present in the urine of chronic alcoholics is a novel ethyl glucuronide which can be readily distinguished and separated from the commonly-known carbohydrate saccharides used as standard controls, preferably in the chloroform/methanol/acetic acid/water solvent mixture described above and related in TABLE 1 and in FIG. 1.

Figure 2A:
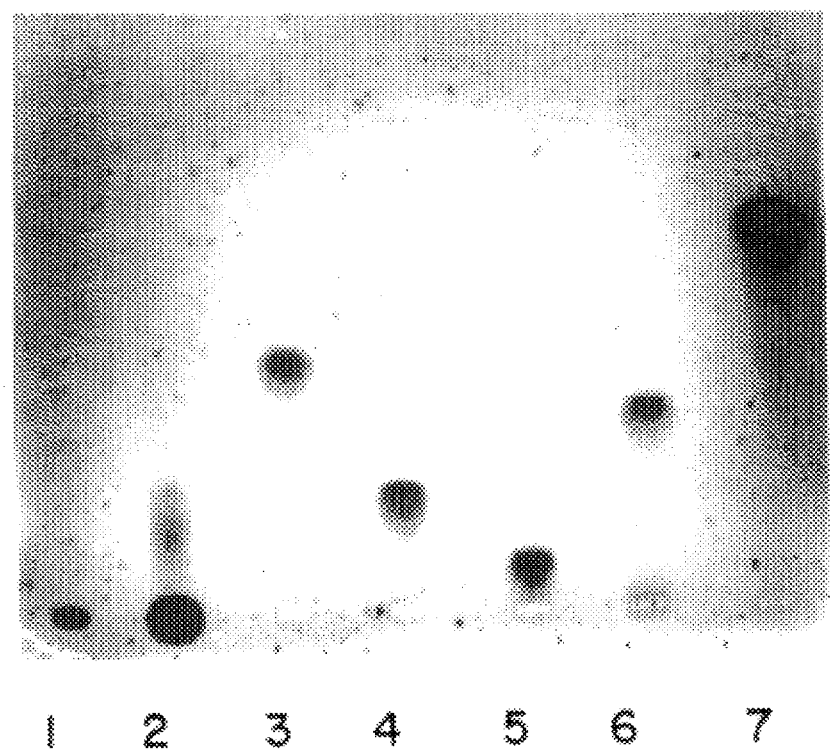
FIGS. 2A and 2B show a thin layer chromatograph developed in a solvent mixture of acetone/chloroform/water in the proportions of 85:10:5, by volume, and then reacted with diphenylamine/aniline/phosphoric acid (DAP) reagent. Lane I shows the inability of this solvent system to resolve the alcohol-specific ethyl glucuronide as evidenced by the lack of migration of ethyl glucuronide present in a urine sample from a chronic alcoholic individual. Lane 2 shows the migration of one DAP-reactive glucuronic acid lactone biproduct of acid hydrolysis of the ethyl glucuronide of lane 1. Lanes 3–7 show standard saccharides run in parallel as controls. Lane 3: glucose; Lane 4: sucrose; Lane 5: lactose; Lane 6: galactose; Lane 7: xylose. For all samples shown in FIGS. 2A and 2B, the mobility (in cm) and $R_f$ values correspond with the values shown in TABLE 3 herein.
Figure 2B:
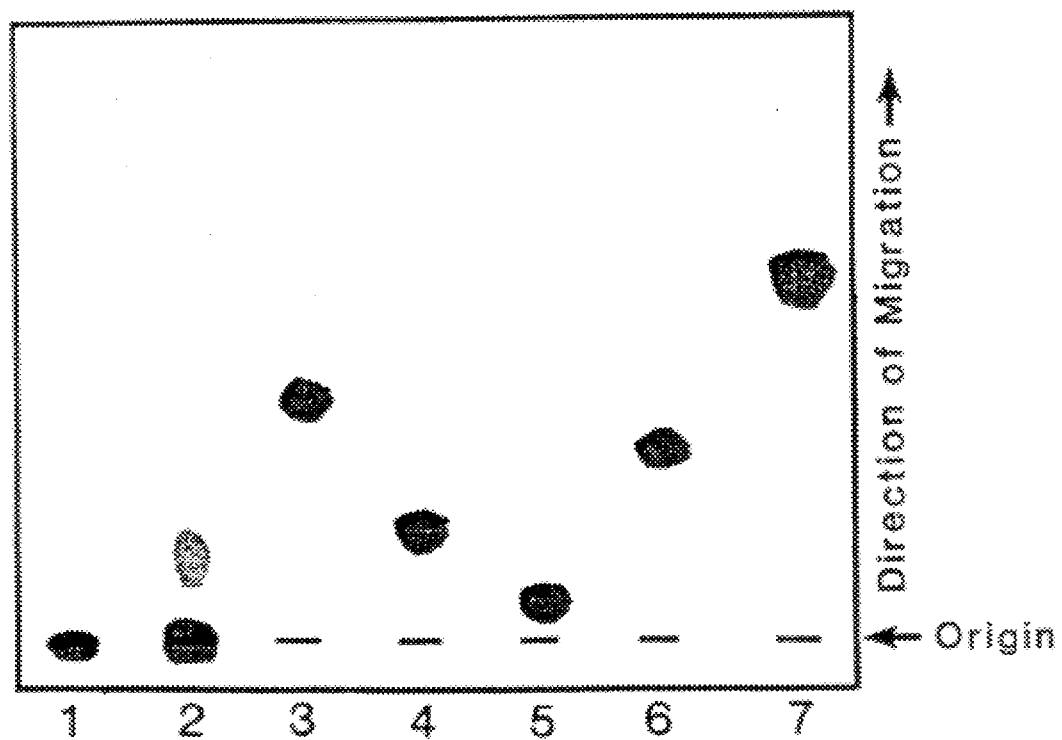

In contrast, in a solvent mixture of acetone/chloroform/water in the proportions of 85:10:5, by volume, the non-acid-hydrolyzed, ethyl glucuronide does not move from its position at the origin on the TLC plate (FIG. 2A, lane 1), and even after acid-hydrolysis, only the glucuronic acid lactone reaction product of acid hydrolysis moves away from the origin as related in lane 2 of FIG. 2 and in TABLE 3.

TABLE 3

TLC Solvent System: Acetone/Chloroform/Water (85:10:5, by volume)

| Sample | Mobility from Origin (cm) | $R_f$ Value |
|---|---|---|
| Alcohol-specific carbohydrate #1 | 0 | 0 |
| Acid-hydrolyzed, alcohol-specific carbohydrate components from #1 (1 component) | 0; 2.0 | 0.13 |
| Glucose | 5.2 | 0.35 |
| Sucrose | 2.4 | 0.16 |
| Lactose | 1.0 | 0.07 |
| Galactose | 4.2 | 0.28 |
| Xylose | 8.1 | 0.50 |

In the chloroform/methanol/acetic acid/water solvent mixture, the alcohol-specific ethanol glycoconjugate in a chronic alcoholic sample, and one of the three, acid-hydrolyzed carbohydrate components appear to have a migration position or $R_f$ value similar to a known monosaccharide such as galactose, as reflected in TABLE 1. However, other solvent mixtures (such as chloroform/methanol/water in TABLE 2) used for chromatography development and separation show clear migration position differences and $R_f$ value differences between the alcohol-specific glycoconjugate and the standard carbohydrates used as controls. Furthermore, mass spectophotometric analysis of the isolated and acid-hydrolyzed glycoconjugate has shown that this ethyl glucuronide is distinct from any of the commonly-known saccharides used as controls. Therefore, it is readily apparent that the alcohol-specific ethyl glucuronide is capable of being distinguished from standard, control carbohydrates which are unrelated to long-term alcohol consumption.

It should be clear to the skilled artisan that modifications of the above-described isolation and purification procedures using methods and reagents known in the art would also permit the isolation and purification of the alcohol-specific ethyl glucuronide from samples without affecting the scope of the present invention.

Assay Methods for Determining Chronic Alcoholism

In one embodiment, a simple, qualitative assay method is used to detect the chronic alcoholism-related ethanol glycoconjugate in test samples. A DAP reagent comprising a mixed solution of diphenylamine, aniline, and phosphoric acid (DAP) reacts chemically (i.e. calorimetrically) with the alcohol-specific ethyl glucuronide found in test samples and produces a definite color, typically in the visible blue range. DAP reagent is preferably prepared by mixing diphenylamine, aniline, and phosphoric acid reagents with acetone such that the resulting solution contains about 2% diphenylamine, about 2% aniline, and about 15% phosphoric acid in a given final volume of the DAP reagent.

Any practical volume of DAP reagent can be prepared at one time, either as a stock solution or to be used at the time of assay, although from about 5 ml to about 1000 ml of DAP reagent is reasonable to prepare at one time to avoid waste and to maintain freshness of the DAP reagent. Smaller volumes of DAP reagent, preferably about 50 ml to about 200 ml, can be prepared at regular intervals to avoid chemical breakdown of the individual reagent components and subsequent loss of activity in the present assays. Preferably, DAP reagent is stored in a dark container in the cold (e.g. approximately 4° C.) for optimal preservation of the reagent's performance in the present assays. Suitable amounts of diphenylamine are from about 1.5 g to 2.5 g, preferably 2 g, in a total volume of 100 ml; suitable amounts of aniline are from about 1.5 ml to 2.5 ml, preferably 2 ml in a total volume of 100 ml; suitable amounts of phosphoric acid used are from about 12 ml to 18 ml, preferably 15 ml, in a total volume of 100 ml. Acetone is typically used to make up the final total volume of the DAP reagent to the desired or preferred amount. One skilled in the art will know that the individual components of the DAP reagent are added in amounts effective to result in their desired final concentrations in the DAP reagent as described above.

In a preferred embodiment, a fluid sample to be tested is applied onto or contacted with the surface of an absorbent substrate such as thin layer chromatography (TLC) substrate. Because of the sensitivity of the assay method, only a small aliquot of the fluid test sample is required to be contacted, spotted, or otherwise applied onto the substrate. Accordingly, the amount of the sample used for assay can be small, i.e., in the range from about 2 µl to about 100 µl, preferably from about 5 µl to about 30 µl. However, the amount of fluid sample assayed by the present methods may be smaller or larger, i.e., in the range of from as little as 1 µl to milliliter amounts. Samples may be also concentrated and an aliquot of the concentrated sample may be used, if desired. The skilled practitioner will recognize that the amount of fluid sample used should be large enough to allow for neat and manageable application onto the absorbent substrate and to permit reaction with the prepared DAP reagent. If other than an absorbent substrate is used as described herein, it is understood that the sample amount may be larger than that used in the described spot or TLC assays.

The substrate containing the applied samples is then dried, and DAP reagent is added or supplied in an amount sufficient to allow a calorimetric reaction to occur after a suitable incubation period. Typically, the amount of DAP added is at least equal to the amount of sample that was originally applied to the substrate, in the range from about 2 µl to about 1.0 ml, preferably from about 5 µl to about 30 µl, but somewhat more DAP reagent than sample is suitable for use. DAP reagent as prepared can also be applied to the substrate containing dried samples by spraying the surface or submerging the substrate so that the samples are wettably contacted with the DAP reagent.

After the addition of DAP reagent, the substrate is preferably dried and is protected by some means, such as by covering with a clean glass plate or the like prior to incubation. Incubation of the samples with the DAP reagent on the substrate is preferably performed in a heated environment such as an conventional oven at about 120° C. for about 10 minutes to about 50 minutes, preferably about 20 to 30 minutes, or in a microwave oven for approximately 60 seconds to approximately 90 seconds.

If the alcohol-specific ethyl glucuronide is present in the sample, a color appears following an appropriate incubation period due to the chemical reaction of the DAP reagent with this novel carbohydrate. Typically, the color produced by the DAP reaction is in the visible blue range, usually deep violet to dark blue indicative of a positive reaction. The region of color can be visualized with the naked eye and can serve as the indicator of chronic alcoholism in those test samples which contain the ethyl glucuronide directly associated with chronic alcoholism. Color may also be detected and determined through the use of a spectrophotometer. No significant color appears in the normal, non-alcoholic, non-diabetic control samples, since the novel carbohydrates of the invention are present in detectable levels only in chronic or excessive alcohol users.

Figure 3A:
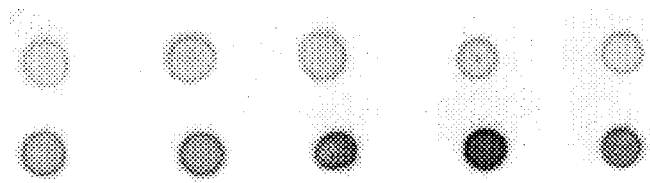
FIGS. 3A and 3B show a spot test for chronic alcohol consumption using human urine from a chronic alcoholic and DAP reagent. The upper spots 1–5 represent urine samples from different, non-alcoholic, normal individuals. Only nonspecific background coloration is observed in spots 1–5, thus indicating a negative reaction. The lower spots 6–10 represent urine samples from different, chronic alcoholics within seven days of their last drink. A dark blue coloration indicative of a positive reaction is observed in spots 6–10.
Figure 3B:
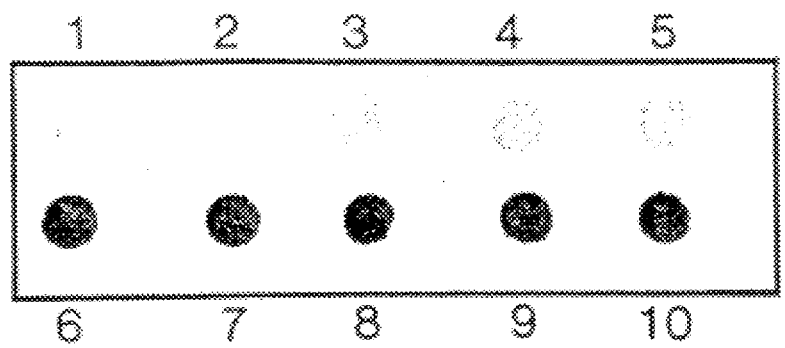

A specific embodiment is a spot assay method for detecting and monitoring chronic alcohol consumption. The spot test provides a rapid, qualitative, objective, and dependable determination of long-term alcohol use. Preferably, a urine sample is used, since obtaining a urine specimen is relatively easy and causes minimal upset to an individual. A small aliquot (e.g. from about 2 µl to about 50 µl) of a urine sample can be applied as a spot onto a thin layer chromatography (TLC) silica gel plate or strip or disk or the like, or other suitable absorbent substrate. One urine specimen provides adequate sample for several assays and for replicate samples to be run each time a test is performed. Sample concentration is not required, but may be carried out if desired or necessary due to large sample volumes. Moreover, the urine test samples may be collected randomly and used immediately after collection, or they may be collected over a given period of time, and then stored frozen at −20° C. or −70° C. until future use. DAP reagent is then added to, or sprayed, or otherwise applied onto the substrate containing the dried spot(s), and the incubation is performed as described above. The spot assay in FIGS. 3A and 3B reflects that urine samples from chronic alcoholics contain the ethanol glycoconjugate which reacts with the DAP reagent, while urine samples from normal, non-alcoholic controls do not, since normal or non-alcoholic urine samples do not contain detectable levels of this novel compound derived from alcohol as determined from the insignificant background levels of staining of the control samples. Quantitatively, the OD values obtained for the five alcoholic samples shown in FIG. 3B are about 8 to 12 times higher than those of the five control, non-alcoholic samples shown in FIG. 3A.

The diphenylamine/aniline/phosphoric acid (DAP) reagent used to detect the novel glycoconjugate associated with chronic alcohol consumption can also detect the high levels of glucose that are indicative of the disease diabetes mellitus, in which glucose found in the urine is overproduced by the liver and under-utilized by other organs of the body. Thus, to categorically distinguish a diabetic individual from a chronic alcoholic, another simple and objective assay which routinely detects glucose in the urine of diabetics can be carried out in parallel with the present assays. As an example, a glucose detection device, such as that described in U.S. Pat. No. 3,992,158 to Przybylowicz et al., issued Nov. 16, 1976, can be used to test an aliquot or portion of the test sample for diabetes. Alternatively, a second fluid sample from the test individual may be provided for the determination of diabetes, if desired or necessary. Since glucose is not the alcohol-specific carbohydrate newly-found and identified in the urine or body fluids of chronic alcohol users by the present assay methods, the secondary test for diabetesassociated glucose confirms, by an independent means, that an individual has diabetes, whether or not that individual is also a chronic alcoholic.

Illustrative examples of absorbent substrates for use in the present assays are porous materials having a mean pore diameter of about 40 A to about 80 A, preferably about 60 A, and a mean particle size of about 0.5 μm to about 20 μm, which are susceptible to absorption and/or traversal by a fluid or liquid medium in response to capillary force. Such substrate materials are generally hydrophilic or are capable of being rendered hydrophilic, and include inorganic powders such as silica, magnesium sulfate, alumina, and the like, as well as polyacrylamide, agarose, polyacrylate, and the like; either used by themselves or in conjunction with other materials, and the like. Substrates derived from cellulose, such as fiber-containing papers and the like, are preferably to be avoided in the present methods because these materials may interfere with the specific reactivity of the DAP reagent and the alcohol-specific glycoconjugate. If necessary, the absorbent material can be attached to or provided in a support. The absorbent substrate can be derivatized, chemically treated or coated, or polyfunctionalized, if so desired. The absorbent material can be a single structure such as a sheet cut into strips or pieces of different shapes and sizes, or it can be particulate material bound to a support or solid surface, such as aluminium, glass, polyester, and similar materials which are commonly used in carrying out thin layer chromatography procedures, for example.

The support for the absorbent substrate, where a support is desired or necessary, will normally be insoluble in aqueous and organic solvents, non-porous, and rigid. The support may be of the same length and width as a strip of the absorbent substrate, but may be larger, such as a chromatography chamber, or smaller. If the support is somewhat larger dimensionally than the strip of the absorbent substrate, the support can serve as a protective housing or casing device for the strip onto which samples are applied, such as would be provided in a kit. A wide variety of organic and inorganic materials, both natural and synthetic, and combinations thereof, may be employed provided that the support does not interfere with the capillary action of the absorbent substrate, or non-specifically bind to components in the assay, or interfere with the calorimetric reaction. Illustrative supports include polymers such as polyethylene, polypropylene, poly(4-methylbutene), polystyrene, polymethylacrylate, poly(ethylene terephthalate), nylon, poly(vinyl butyrate), or glass, ceramics, metals, and the like.

In a variant of the preferred embodiment, the test sample to be assayed can be placed in an container, such as a tube, vial, multi-well or microtiter plate, or other holding means, for example, a container large enough to hold about 0.05 ml to about 20 ml, preferably from 0.1 ml to 5.0 ml. As mentioned previously, the small volume is for convenience and practicality only and does not preclude the use of a substantially larger sample volume or a concentrated sample derived from a larger sample volume. An appropriate amount of DAP reagent can be added to the sample in the container and the resulting color can be visualized and determined following an appropriate incubation period. Alternatively, the DAP reagent can be provided in the container and the sample can be added thereto. Appropriate standard or control samples (i.e. negative control samples such as non-alcoholic samples; non-alcoholic and non-diabetic samples; and positive control samples from known chronic alcoholics, or a solution of purified ethyl glucuronide, or chemically-synthesized 1-O-ethyl glucuronide can be assayed in the same manner as the test sample, and the negative or positive colorimetric results of all samples can be compared to determine if chronic alcoholism is shown in the test sample, after all samples have been subjected to the DAP reagent.

It can be appreciated by one skilled in the art that the simple calorimetric test for chronic alcoholism can be carried out using a single, batch, or continuous assay method for determining the presence of the novel alcohol-specific carbohydrate in body fluids without materially departing from the scope of the invention. Such assay methods may be carried out using a conventional automated sample or clinical analyzer (e.g. the "Boehringer Mannheim/Hitachi 717 System®" or the like, or an automated multi-well plate reader, or the like) that routinely and automatically performs the steps of sample analysis after the requisite reagents are provided and a sample is injected into or otherwise supplied to the appropriate part of the analyzer. Quantitative results from the color-producing step can be automatically determined and recorded by a spectrophotometer which can be an intrinsic part of the automated laboratory instrumentation, or can be attached to the analyzer portion of the instrument.

In another preferred embodiment, a chromatographic test method can be used, preferably ascending chromatography. The chromatographic test is objective and economical, and it allows a quantitative estimation of the levels of alcohol-specific ethanol glycoconjugate using a standard clinical or laboratory densitometric spectrophotometer or densitometry scanner.

Ascending chromatography is preferred and useful, since it separates small molecules such as saccharides or carbohydrates present in fluid samples. Typically, a portion of the sample (from about 2 μl to about 0.2 ml, preferably from 5 μl to about 50 μl), is applied as a spot onto a sheet or strip of absorbent substrate. The absorbent substrate may be a sheet of plastic or glass or aluminium covered (usually on one surface) with a layer of inert absorbent material, such as silica gel, most preferably silica gel G, for the performance of thin layer chromatography (TLC). The thickness of the layer can be from about 100 μm to about 1000 μm, preferably about 200 μm. As discussed hereinabove, cellulose or paper-based substrates are not preferred for use because of their interference with the specificity of the reaction of DAP reagent with alcohol-specific ethanol glycoconjugate.

Preferably, one or more samples is applied to one end of the absorbent substrate, called the "origin". After the sample has dried on the substrate at the origin, the substrate is placed in a chromatography chamber in a vertical position and a mixed solvent containing water (e.g. one or more organic solvents and water) is allowed to permeate the absorbent substrate from the edge of the substrate at which the sample has been applied (i.e. the origin). As the liquid moves across the absorbent substrate in an upward direction by capillary action, the molecules in the sample are separated according to their relative solubilities in the components of the mixed solvent.

Ascending chromatography is preferably carried out in a covered glass chamber that has been previously equilibrated with the mixed solvent, although other types of TLC apparati can also be used. The chromatography substrate can be manually placed inside the developing chamber where it can rest against a wall of the chamber for stability and support or it can be suspended in the chamber via suspension rods or hangers. More than one sheet or strip can be developed in the chamber, if needed or desired.

The chromatography procedure can also be performed in an electrophoretic chromatography chamber which is attached to a power source via electrodes or the like. Electrophoretic chromatography decreases the chromatography running time, since the current, rather than capillary motion, moves the molecules through the developing solvent mixture and vertically upward on the absorbent substrate.

The mixed solvents used in the ascending or thin layer chromatography methods are selected so that one of them is held more strongly than the other by the absorbent substrate, and forms a stationary solvent layer on the surface of the substrate sheet or plate. Various mixed solvents having different polarities are suitable for use in resolving or separating the alcohol-derived ethanol glycoconjugate. One skilled in the art will appreciate that the types of mixed solvents employed and the ratios of the solvent components can vary and still result in appropriate migration and resolution of the glycoconjugate product.

It is important that the mixed solvent used for ascending chromatography allows the alcohol-derived glycoconjugate to migrate away from the origin and allows a clear separation of each of the test and control carbohydrates on the substrate plate. One preferred mixed solvent is chloroform/methanol/water used in a ratio of 65:35:5, by volume. TABLE 2 shows that the alcohol-specific ethanol glyconjugate in urine migrates away from the origin (approximately 3.7 cm) and that the migration distance does not coincide with that of standard carbohydrate saccharides run in parallel as controls; the acid-hydrolyzed products of the glycoconjugate, i.e., glucuronic acid and glucuronic acid lactone, migrate as two entities in this solvent mixture at 1.3 cm and 11.3 cm, respectively. By contrast, it is shown in TABLE 3 and in FIG. 2 that in another mixed solvent comprised of acetone/chloroform/water in the proportions of 85:10:5, by volume, the alcohol-specific ethanol glycoconjugate does not migrate away from the origin, while the standard monosaccharides migrate a distance of from about 1 cm to over 8 cm from the origin. If the novel ethanol glycoconjugate is first isolated by thin layer chromatography, removed from the plate, and acid-hydrolyzed as described above, only the resulting glucuronic acid component migrates very poorly in this mixed solvent.

Figure 1B:
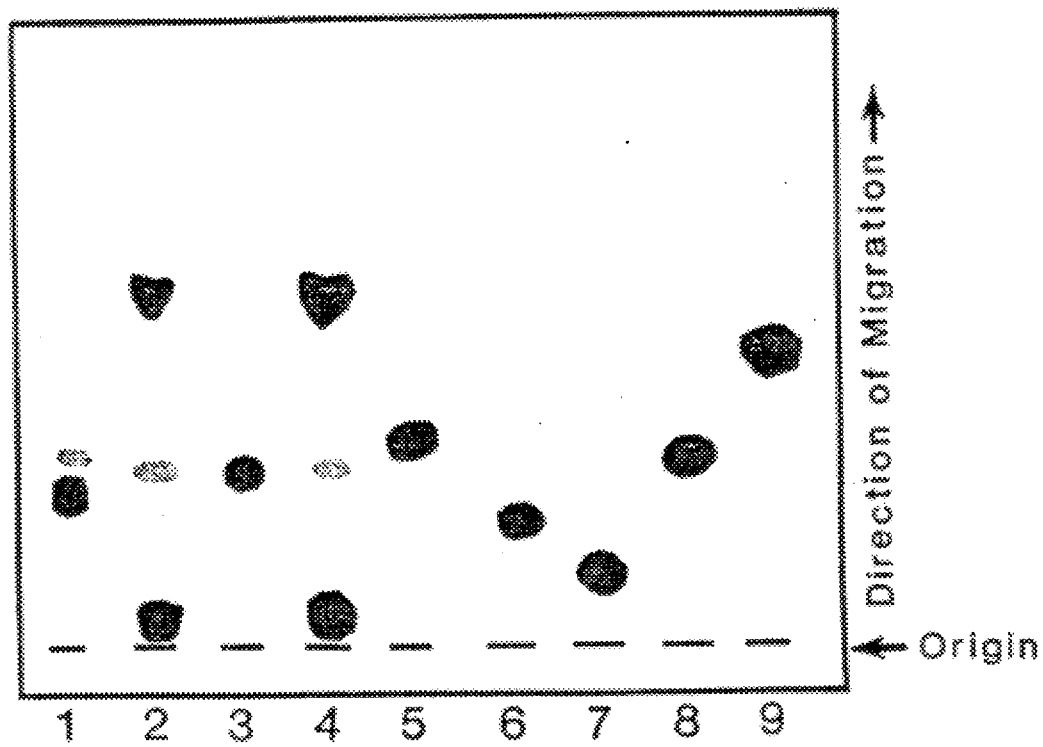

Another prefer red mixed solvent used to identify and detect the alcohol-derived ethyl glucuronide is a chloroform/methanol/acetic acid/water solvent mixture prepared in the proportions of 50:20:6:1.5, by volume. In TABLE 1 it is shown that in this mixed solvent, the alcohol-specific ethyl glucuronide (generically termed "carbohydrate #1 and #2") move s as one spot a considerable distance away from the origin (approximately 4.2 cm or 4.3 cm) and corresponds to migration and $R_f$ values which have been shown to be different from the standard sugars run in parallel as controls. In addition, as shown in FIGS. 1A and 1B, the use of this solvent resolves the isolated acid-hydrolyzed products of the ethyl glucuronide into three, distinct carbohydrate component spots with distinct $R_f$ values. As previously described, the fast moving component in lanes 2 and 4 of FIG. 1A is glucuronic acid lactone, the slowest moving component is glucuronic acid, and the middle component is believed to be incompletely hydrolyzed or non-hydrolyzed material.

Specifically, in the ascending chromatography assay, molecules such as t he alcohol-specific ethyl glucuronide equilibrate between the stationary and moving solvents in each region of the chromatography plate, sheet, or strip. Those molecules that are most soluble in the strongly-absorbed solvent are relatively retarded because they spend more time in the stationary layer, while those molecules that are most soluble in the other solvents move more quickly. After a given period of time for "running" or "developing" the chromatograph, preferably from about 10 minutes to more than 60 minutes, depending on the siz e of the substrate plate, sheet, or strip, but most preferably from about 15 minutes to about 30 minutes, the sheet or strip of absorbent substrate is dried and then stained or otherwise reacted with reagents allowing a colorimetric determination of the exact location of the various molecules. Each component in a sample moves in a line vertical to the original spot at the origin and perpendicular to the solvent front, producing a spot similar in shape to the original sample spot. Each compound moves along the absorbent substrate in direct proportion to the distance moved by the mixed solvent. This is a constant value for each compound or component in a particular solvent mixture and is known as the $R_f$ value.

It will be understood by the practitioner that modified ratios of the mixed chromatographic solvents may be employed without affecting the scope of the present invention. In addition, other mixed solvents having varying degrees of polarity may potentially be formulated to identify, separate, and isolate the ethyl glucuronide in an alcoholic's sample.

In the chromatographic embodiments, the diphenylamine/aniline/phosphoric acid (DAP) reagent is applied to the dried chromatograph which has first been developed in the mixed solvent system. Preferably, the DAP reagent is sprayed onto the surface of the chromatograph for convenience and for facility in wetting the appropriate chromatograph surface area with the DAP reagent in a controlled manner; however, other modes of wettably contacting the chromatograph with the DAP reagent are envisioned, for example, immersing, dipping, or pipetting, either automatically or manually, or the like.

In a specific embodiment, both positive control, negative control, and test samples from individuals being tested for chronic alcoholism are applied to the absorbent substrate and all samples are run in parallel to permit a direct comparison of the colorimetric results of the control samples with the test sample or samples after the application of DAP reagent. Alternatively, test samples can be run separately on one TLC substrate, and the standards can be run on another TLC substrate, either in the same chromatography chamber or in parallel chambers, and the colorimetric results of the control and the test samples can be compared after reaction with DAP reagent.

In another embodiment, high performance liquid chromatography ("HPLC") may be used to identify whether or not a particular sample contains the novel ethanol glycoconjugate and its ethyl glucuronide component found to be directly associated with chronic alcohol consumption. For conducting the HPLC analysis, phenacyl ester derivatives of the samples are prepared as described in Example VI. Thus, HPLC analysis may be used to determine whether or not a sample contains the novel ethyl glucuronide and, ultimately, whether or not the individual providing the sample is an alcoholic. HPLC is a sensitive and reliable method for detecting the novel alcoholspecific biomarker. The results obtained using HPLC detection are shown in FIGS. 8A and 8B. Modifications of the HPLC conditions exemplified may be made by those skilled in the art without affecting the spirit or scope of the invention.

For all assay methods described, appropriate controls are usually provided or control assays are preferably run in parallel so that the results obtained with the test sample(s) can be compared with samples from a chronic alcoholic, a recovering alcoholic, and/or a normal, non-diabetic, non-alcoholic individual. The simple spot assay is rapid, since a calorimetric reaction with the DAP reagent will readily occur if the test sample contains the ethanol glycoconjugate in a chronic alcoholic sample. In all cases, a corresponding test for glucose indicative of diabetes mellitus can be conducted independently, if desired or needed.

To distinguish between unusually dilute and concentrated urine samples when carrying out the assays, urinary creatinine concentration is customarily and preferably monitored in all samples using standard methods such as the alkaline-picric acid method described by Yatzidis, H. (1974). *Clin. Chem.* 20:1131–1134. If necessary or desired, results from the present assays can be normalized to the urinary creatinine value. When required, samples are further concentrated or diluted as necessary prior to the assay. The normalization of values to a standard protein such as creatinine is a common practice in clinical chemistry. Normalization is routinely carried out in a variety of assays involving experimental samples. Since urine is used as an exemplary test sample, urinary creatinine concentration is used for normalization. It is known that normalizations are conventionally performed to account for differences in volume or size of particular samples, among other parameters. For example, when urine is used to test for the presence of the alcohol-specific glycoconjugate, the volume of urine may vary widely, depending on the fluid intake of the individual being tested. In the case of alcoholics, a person who drinks beer versus a person who consumes the same amount of alcohol as hard liquor will have divergent volumes of urine, hence the need for some type of standardization or normalization against a given standard whose amount does not vary significantly in the sample. If desired, normalization to other appropriate protein standards could readily be used for body fluid samples other than urine.

If the ethyl glucuronide specific to chronic alcoholism is to be detected or monitored in body tissues or fluids other than urine, samples will be appropriately collected, processed, and then concentrated or diluted as necessary before carrying out the assay. For example, for the preparation of a tissue sample from which to assay for the novel ethanol glycoconjugate, it is within the purview of those skilled in the art to homogenize a tissue sample in an appropriate buffer (e.g., physiologic saline, phosphate buffered saline, and the like) using either a manual or automatic homogenizer or grinding apparatus. Appropriate care should be taken to prepare the sample as efficiently as possible, preferably on ice or in the cold, to avoid degradation. In addition, protease and other inhibitors may be added, if desired. After homogenization and centrifugation, the soluble portion of the homogenate is used as the material for analysis in the spot, TLC, or HPLC assays.

Preparation of Antibodies for use in Detecting the Alcohol-derived Ethyl Glucuronide Specific to Chronic Alcohol Consumption The purified or semi-purified alcohol-specific ethyl glucuronide obtained from the isolation procedures as described herein can be used in conjunction with an appropriate carrier, if necessary, in a composition as an immunogen to generate polyclonal antibodies or monoclonal antibodies in a host animal of choice, using standard immunological techniques and procedures known to those skilled in the art. In addition, the 1-O-ethyl glucuronide may be synthetically prepared for use in the immunogenic composition. That the novel carbohydrate may be chemically synthesized allows the production of large amounts of immunogenic material, if needed or desired, especially for subsequent booster immunizations.

The antibodies so produced will have specificity to one or more of the epitopes present on the alcohol-specific carbohydrate molecule. The term "epitope" as used herein is meant to include any determinant on a molecule that is responsible for specific interaction with or binding to an antibody molecule. Epitope determinants usually consist of surface groupings of molecules (such as amino acids or carbohydrate side chains) and often have chemically active and three-dimensional structural characteristics as well as specific charge characteristics. Such antibodies are also useful, for example, in further detection, diagnostic, and characterization assays to identify and monitor excessive alcohol intake.

Polyclonal Antibodies

The procedure for obtaining polyclonal antibodies is illustrated herein in general terms: Polyclonal antibodies are generated most simply by injecting an immunogenic composition comprising purified or semi-purified ethyl glucuronide or synthetically prepared 1-O-ethyl glucuronide (called antigens or immunogens) into an animal such as a mouse, rabbit, sheep, or goat, and the like. The initial immunizing dose of antigen is injected into the animal, either with or without an adjuvant, such as alum, and with or without an immunostimulant, such as 3-deacylated monophosphoryl lipid A or 3D-MPL. The animal is allowed to rest, and several additional injections (usually at smaller doses than the original immunizing dose) are administered to the animal at one or more of a variety of sites over a period of weeks or months, with one to two week rest periods between injections. The subsequent injections of antigen are called "boosts". Between boosting injections of antigen, the animal's serum is tested to determine evidence of in vivo-produced antibodies which are reactive with epitopes on the alcohol-specific ethanol glycoconjugate or ethyl glucuronide. To this end, a sample of blood is obtained from the animal, and the plasma fraction is isolated and assayed to determine the level (i.e. titer) of antibodies in the serum having reactivity toward determinants (i.e. epitopes) on the alcohol-specific ethyl glucuronide using immunobiological methods known to those skilled in the art.

The polyclonal antiserum contains a heterogeneous mixture of antibodies, each produced by a different antibody-secreting B cell (B lymphocyte). Different antibodies recognize and bind to various parts of the antigen molecules; other antibodies in the polyclonal antiserum bind to any impurities that might be present in the antigen preparation. Thus, the specificity of the polyclonal antiserum can be increased by removing from the preparation the unwanted antibodies that bind to extraneous molecules through the use of an affinity column. Examples of affinity columns include, but are not limited to, known carbohydrates coupled to inert resin (or particles coating a resin) which will bind all antibodies directed to the commonly-found, non-alcohol related carbohydrates. However, the alcohol-related antibodies will be collected in the flow-through from the column, as they will not specifically react with the known carbohydrates bound to the column. Alternatively, alcohol-specific ethyl glucuronide purified or chemically synthesized and coupled to inert resin produce an affinity resin that will specifically bind all antibodies which react with the unique, alcohol-associated ethyl glucuronide of the invention. Specific antibodies can be eluted off the column in discrete fractions with appropriate buffer systems.

Affinity-purified polyclonal antibodies can be very specific for a given antigen and can be used to detect the alcohol-specific carbohydrate in various samples employing a variety of immunological detection methods and assays which are discussed below.

Protocols for producing and purifying polyclonal antibodies are well known in the art and can be found in the following representative publications: Parish, H. J. (1965). *A History of Immunization*. Livingstone; Mishell, B. and Shiigi, S. (Eds.), (1980). *Selected Methods in Cellular Immunology*. W. H. Freeman & Co., San Francisco, Calif.; Eisen, H. N., (1964). *Meth. Med. Res.,* 10:94.

Hybridoma Cell Lines and Monoclonal Antibodies

Hybridoma technology allows the production of monoclonal antibodies of a single specificity to be obtained in virtually unlimited amounts. Monoclonal antibodies obviate the problem of heterogeneity that is intrinsic to polyclonal antibody preparations.

For monoclonal antibody production, animals, preferably mice or rats, are immunized and boosted with the alcohol-specific carbohydrate immunogen in the same manner as that described for the production of polyclonal antibodies. When it is determined that an animal is producing a significant in vivo antibody titer reactive with the alcohol-specific ethyl glucuronide, hyridoma cell lines are produced by the following illustrative procedure, which is not intended to be strictly limited to this method only. Modifications and variations to the general procedures of monoclonal antibody production are well-known in the art. Reference is made to the following for a sample of reviews and commentary on the production of hybridoma cell lines by somatic cell fusion: Kohler, G. and Milstein, C. (1975). *Nature,* 256:495; Kohler et al. (1976). *European J. Immunol,* 6:511-519; Croce, C. et al., (1982). *Somatic Cell Genetics,* Plenum Press; Olsson et al., (1980). *Proc. Natl. Acad. Sci. (USA),* 77:5429; "Lymphocyte Hybridomas", (1978). Ed. F. Melchers et al., Springer-Verlag, N.Y.; *Science,* 208: 692 (1980); *JAMA,* 242:2161 (1979); European Patent Application No. 0044441, published Jan. 27, 1982, to Mollinaro, C. and Nakamura, R. M., Diamond, B. et al., (1981). *New Eng. J. Med.,* 304:1344; Hurrell, J. G. R. (Ed.), (1982). CRC Press; Melchers, F. et al., (1978). *Curr. Top. Microbiol. Immunol.* 81:Preface; and McMichael, A. J. and Fabre, J. W., (1982). Academic Press.

A. Preparation of the alcohol-specific carbohydrate for use as immunogen

An alcohol-specific carbohydrate immunogen can be prepared by purifying or semi-purifying the alcohol-specific ethyl glucuronide as described above. In addition, 1-O-ethyl glucuronide may be prepared synthetically as described and used as an immunogen. The purified carbohydrates can be used in a composition with or without adjuvant and immunostimulant as an immunogen. If the purified carbohydrate is of insufficient size to elicit an immune response alone, the compound may be conjugated to appropriate carrier proteins, such as albumin, keyhole limpet hemocyanin, detoxified toxin proteins, bacterial cell wall proteins, viral proteins, or other types of carrier molecules, using chemical coupling methods known in the art and illustrated in the following publications: Mishell, B. and Shiigi, S. (Eds.), (1980). *Selected Methods in Cellular Immunology,* Chapter 16, W. H. Freeman & Co., San Francisco, Calif.; Weir, D. M. (Ed). (1978). In *Handbook of Experimental Immunology,* third edition, Vol. I, Blackwell Scientific Publications, Oxford; Eisen, H. N. et al., (1953). *J. Am. Chem. Soc.,* 75:4583; Garvey, J. S. et al., (1977). *Methods in Immunology,* W. A. Benjamin, Reading, Mass.; Nisonoff, A., (1967). *Methods in Immunology and Immunochemistry,* Academic Press, New York and London. Further, those skilled in the art will be aware that modifications may be made to the novel carbohydrate component of the immunogen in order to facilitate coupling, binding, or immunogenicity, and the like, provided that the antibodies generated from the immunization(s) ultimately recognize and react with (i.e., bind to, preferably with specificity) the ethyl glucuronide to detect chronic alcoholism.

B. Immunization

A Balb/c or other appropriate mouse strain (approximately 8–12 weeks old) is injected intraperitoneally with a suitable amount of the carbohydrate immunogen or immunogen conjugate with or without adjuvant and immunostimulant. A concentration range for the initial dose of immunogen is from about 20 micrograms (µg) to about 200 µg, preferably about 50 µg to about 100 µg. Four to eight weeks later, the mouse is re-injected intraperitoneally with about 20 µg to about 100 µg of the immunogen with or without adjuvant. Subsequent booster injections with about 20 µg to about 100 jig of immunogen are repeated every two to three weeks, if desired. Ten days after the final injection, the mouse is bled and the serum is tested for antibodies to the alcohol-specific carbohydrate compounds. Three to four days prior to fusion, the mouse is boosted intraperitoneally with about 10 µg to 20 µg of alcohol-specific carbohydrate immunogen or conjugate without adjuvant.

C. Isolation of spleen cells

A mouse is sacrificed and the spleen is removed asceptically into a sterile tissue culture dish containing serum-free cell culture medium, such as Dulbecco's Modified Essential Medium (DMEM) (approximately 5 ml) with high glucose. The spleen is cut into fragments and spleen cells are removed from the splenic capsule, for example, by gently grinding the pieces of spleen between the frosted ends of two sterile microscope slides. The isolated cells are resuspended with a pipet and then filtered through a piece of sterile nitex screening fabric (110 µ) into a sterile test tube. The tube is centrifuged at 4° C. at approximately 350×g for about 5 to 7 minutes. The supernatant is removed and the cells are resuspended by gentle pipetting or tapping of the bottom of the tube. If desired, the spleen cells can be treated with Tris-buffered (10 mM, pH 7.2) ammonium chloride (0.17M) to remove red blood cells.

To enhance the number of B lymphocytes having specific reactivity toward the alcohol-specific carbohydrate immunogen, isolated spleen cells can be cultured sterilely in vitro in the presence of nanogram to microgram amounts of specific alcohol-associated carbohydrate immunogen using the basic procedure as detailed in Morrison, D. K. et al., (1985). *J. Virology,* 55:670–680. Antigen-stimulated spleen cells cultured in the presence of specific immunogen for one week to ten days can then be fused to myeloma cells as indicated below.

D. Myeloma cells

Several different types of myeloma cell lines from different species are available for use in hybridoma technology. An appropriate myeloma cell line, such as the SP2/0 Ag 14 Schulman et al. (1978). *Nature* 226:269) or X63-Ag8.653 (Kearney et al. (1979) *J. Immunology,* 123:1548) murine myeloma cell lines, is grown in DMEM supplemented to contain 10% fetal bovine serum (FBS) with or without 8-azaguanine (e.g. $10^{-4}$M). An example of a suitable rat myeloma cell line is Y3-Ag1.2.3(Galfre et al. (1979). *Nature* 277:131). Suitable human myeloma cell lines such as that described in U.S. Pat. No. 4,594,325 to R. L. Lundak, issued Jun. 10, 1986, can also be used as fusion partners in hybridoma cell line production. Optimally, myeloma cells in mid-log growth are used as fusing partners.

E. Hybridization procedure

The procedure used for the generation of hybridoma cells is provided for illustrative purposes and is by no means limited to the general method disclosed. A slightly modified method described in Gefter et al., (1977). *Somatic Cell Genetics* 3:231 is provided by example:

Myeloma cells (typically $2 \times 10^7$ cells washed twice in serum-free medium) are mixed with approximately $1 \times 10^8$ spleen cells prepared as described above, and the cell mixture is centrifuged. After all of the liquid is aspirated, the cells are resuspended in a solution of about 25% to about 40% PEG (polyethylene glycol MW1000), preferably 30%, in serum-free DMEM. The cells are incubated in this solution for about 10 minutes. During this 10 minute incubation, the cells are centrifuged at approximately 800 rpm (revolutions per minute) for three minutes. After about eight minutes have elapsed, the fusion reaction is quenched by diluting the cell mixture with serum-free medium (about 5 ml), and the cells are washed once in this medium. The cells are washed a second time in medium such as DMEM supplemented to contain essentially 10% FBS and non-essential amino acids preparation, glutamine, sodium pyruvate (and 10% NCTC 109 medium, bovine insulin (20 I.U./ml), and oxaloacetate (1 mM, if desired), and are finally resuspended in about 40 ml of the same medium either in petri dishes or in tissue culture flasks. The cells are incubated overnight at 37° C. in a humidified atmosphere containing 5% to 10% $CO_2$.

F. Cloning procedure

The following day, the cells are collected, pelleted by centrifugation, and resuspended in 80 ml of the above-described plating medium containing hypoxanthine (e.g. $1 \times 10^{-4}$M), aminopterin (e.g. $4 \times 10^{-6}$ M), and thymidine (e.g. $1.6 \times 10^{-5}$M), called HAT medium as described in *Science* 145:709 (1964). The cells are distributed into 96-well, flat-bottom microtiter plates at approximately 0.1 ml/well. The cells are incubated in these plates at 37° C. in a humidified atmosphere containing 5%–10% $CO_2$ for seven to ten days. At the end of seven days, the cells are fed by adding HT medium (i.e. HAT without aminopterin) to the culture wells; the cultures are fed in the same manner at weekly intervals. If desired, the spleen cells may be co-incubated with irradiated feeder cells such as bone marrow cells or thymus cells, which serve to condition the medium and optimize the growth of the fused hybridoma cells. Culture wells are examined daily to determine cell growth and viability, and to observe the appearance of hybridoma clones in the wells.

G. Screening Procedure

The culture fluid from wells showing growth of hybridoma cells is collected and tested (screened) for the presence of antibodies that bind specifically to the alcohol-specific carbohydrates. To this end, the purified alcohol-specific carbohydrates can be bound to a solid substrate or support such as the wells of a polyvinylchloride tissue culture plate or to a nylon membrane (e.g. GeneScreen or Nitrocellulose) to perform an immunoassay screening procedure either by ELISA, by other immunoassay methods, or by a blotting method (e.g. dot blot, slot blot, or the like). After blocking nonspecific binding sites with buffer containing protein such as albumin, culture supernatants from various hybridoma culture wells are added to the carbohydrates immobilized onto the solid substrate, and incubated to allow binding to occur.

After an appropriate incubation period, the substrate is washed in buffer several times to remove all unbound material. A labeled second antibody from the appropriate species and of the appropriate immunoglobulin isotype is then added to the substrate. The secondary antibody can be enzymatically or radioisotopically labeled. If the culture fluid being tested contains monoclonal antibodies which have specificities for and bind to the alcohol-specific carbohydrates bound to the solid substrate, these secondary antibodies will, in turn, specifically bind to the monoclonal antibodies. Binding can be detected by adding appropriate substrate, if the secondary antibody preparation is enzymatically labeled, or by counting in a gamma or scintillation counter, if the secondary antibody preparation is labeled with radioisotope. Routine protocols for the types of screening methods and procedures discussed herein can be found in the following representative references: Mishell, B. and Shiigi, S. (Eds.), (1980). *Selected Methods in Cellular Immunology*, W. H. Freeman & Co., San Francisco, Calif.; Yelton, D. E. and Scharff, M. D. (1981). *Annu. Rev. Biochem.*, 50:657–680; Kennett, R. H., McKearn, T. J., and Bechtol, K. B. (Eds.), (1982). *Monoclonal Antibodies*: "Hybridomas: A New Dimension in Biological Analyses", Plenum Press, New York.

Culture fluids showing a positive reaction in the screening procedure are re-tested several days later. Hybridoma cells that secrete antibodies which react specifically with the alcohol-specific carbohydrate are rigorously subcloned by limiting dilution in 96-well flat-bottom tissue culture plates in HT medium. The culture fluids from wells containing cells showing clonal cell growth are re-tested several times for antibody secretion as previously described.

Subclones which secrete antibodies of the desired specificities are expanded in vitro, and then in vivo in mice primed with pristane (2,6,10,14-tetramethylpentadecane) to generate specific monoclonal antibodies in ascites fluid to yield abundant amounts (i.e. milligrams) of the monoclonal reagents which may then be further purified using methods known in the art.

After isolating a high titer polyclonal antiserum, or cloning hybridoma cell lines which have been screened and found to produce monoclonal antibodies of the desired specificity(ies), the antibodies can be further purified, using the methods discussed above for polyclonal antibody purification. Antibodies which react specifically with the novel alcohol-specific glycoconjugate can be employed to purify this novel carbohydrate from a starting sample and to carry out many types of immunoassays. The immunoassays utilizing polyclonal and monoclonal antibodies can be direct or indirect competitive or sandwich types of immunoassays. Immunoassays can be performed as solid-phase assays or in solution and can use either radioisotope or enzymatic detection systems. It is well known in the art that all immunoassays depend on the formation of antibody-antigen immune complexes. The various permutations on immunoassay methods and techniques are not described herein, as they are well known to those skilled in the art. A representative description of immunoassay procedures is found in the following references: *Methods in Enzymology Guide to Protein Purification*, (1990). Ed. M. P. Deutscher. *Vol.* 182, Chapter 53, "Immunoassays" by C. W. Parker. Academic Press, Inc. San Diego, Calif.; and in Hunter, W. M. (1978). In D. M. Weir (Ed.) *Handbook of Experimental*

*Immunology*, third edition, *Vol. I*, Blackwell Scientific Publications, Oxford; etc. for detecting the alcohol-specific ethyl glucuronide via one-step or multi-step immunoassays which could also be provided in the form of a kit.

For purposes of the immunoassays, the anti-alcohol-specific carbohydrate antibodies can be immobilized or labeled. The antibodies can be bound to many carriers for immobilization. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble. Those skilled in the art will know many other suitable carriers for binding the antibodies, or will be able to ascertain such, using routine experimentation.

One or more of the antibodies can be coupled with a detectable label such as an enzyme, radioisotope, fluorescent compound, chemiluminescent compound, or bioluminescent compound. Those of ordinary skill in the art will know of other suitable labels for binding to the antibodies or will be able to ascertain such using routine experimentation. In addition, the coupling of these labels to the antibodies can be done using standard techniques commonly known to those skilled in the art.

The antibodies can be bound to an enzyme. The enzyme, when later reacted with its substrate, will produce a chemical moiety which can be detected by spectrophotometric or fluorometric means, for example. Examples of enzymes which can be used to detectably label antibodies are malate dehydrogenase, staphylococcal nuclease, delta-5-steroid isomerase, yeast alcohol dehydrogenase, alpha-glycerophosphate dehydrogenase, triose phosphate isomerase, alkaline phosphatase, asparaginase, glucose oxidase, beta-galactosidase, ribonuclease, urease, catalase, glucose-6-phosphate dehydrogenase, gluco-amylase, and acetylcholine esterase.

The presence of an antibody can also be detected by labeling it with a radioactive isotope. The presence of the radioisotope could then be determined by such means as the use of a gamma counter or a scintillation counter. The antibodies can also be detected by labeling them with a fluorescent compound (i.e. a dye). When the fluorescently-labeled antibody is exposed to light of the proper wavelength, its presence can then be detected due to fluorescence of the dye. Among the best known fluoresecent labeling compounds are fluorescein isothiocyanate, rhodamine, phycoerythrin, phycocyanin, allophycocyanin, o-phthaldehyde, and fluorescamine.

An antibody can also be detected by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, aromatic-acridinium ester, imidazole, acridinium salt, and oxalate ester.

In a similar manner, a bioluminescent compound may also be used to label the antibody. Bioluminescence is a special type of chemiluminescence which is found in biological systems and in which a catalytic protein increases the efficiency of the chemiluminescent reaction. The presence of a bioluminescent binding partner would be determined by detecting the presence of luminescence. Important bioluminescent compounds for purposes of labeling are luciferin, luciferase, and aequorin.

The antibodies for use in immunoassays are ideally suited for the preparation of a kit. Such a kit may comprise a carrier means being compartmentalized to receive in close confinement one or more container means such as vials, tubes, and the like, each of the container means comprising one of the separate elements to be used in the method.

For example, one of the container means may comprise a first antibody bound to an insoluble or partly soluble carrier. A second container may comprise soluble, detectably-labeled second antibody, in lyophilized form or in solution. The carrier means may also contain a third container means comprising a detectably-labeled third antibody in lyophilized form or in solution. Such a kit can be used in "sandwich" immunoassays for detecting the chronic alcohol-specific carbohydrates in test individuals. For example, see David et al., U.S. Pat. No. 4,376,110. It is apparent to those skilled in the art that other immunoassay permutations are suitable for utilizing the antibodies directed against the novel alcohol-specific carbohydrates.

Single chain antibodies expressed in prokaryotic microorganisms (Davis, G. T. et al., (1991). *Biotechnology*, 9:165; Pluckthun, A., (1990). *Nature*, 347:497; Ward, E. S. et al., (1989). *Nature*, 341:544) could be an alternative procedure for producing antibodies having specificity for the novel carbohydrates specifically associated with chronic alcoholism. In addition, chimeric antibodies or "humanized" (i.e., nonimmunogenic in humans) antibodies may be produced, for example, by replacing an immunogenic portion of an antibody with a corresponding, but nonimmunogenic portion (i.e., chimeric antibodies). Chimeric antibodies are described in U.S. Pat. No. 4,816,567 and would be suitable for use. Other examples of chimeric antibodies may be found in Robinson et al., International Patent Application 184,187; Taniguchi, M., European Patent Application 171, 496; Morrison et al., European Patent Application 173,494; Neuberger et al., PCT Application WO 86/01533; Cabilly et al., 1987, *Proc. Natl. Acad. Sci. USA*, 84:3439; Nishimura et al., 1987, *Canc. Res.*, 47:999; Wood et al., 1985, *Nature*, 314:446; Shaw et al., 1988, *J. Natl. Cancer Inst.*, 80:1553; Oi et al., 1986, *BioTechniques*, 4:214.

Exemplary antibodies for use include intact antibody (i.e., immunoglobulin) molecules, substantially intact antibody molecules, and those portions of an immunoglobulin molecule containing the paratope, including antigen binding fragments produced from intact antibodies known in the art as Fab, Fab', F(ab')$_2$, and F(v). Fab and F(ab')$_2$ portions of antibodies are prepared by the proteolytic reaction of papain and pepsin, respectively, on substantially intact antibodies by methods that are well known (see U.S. Pat. No. 4,342,566 to Theofilopolous and Dixon).

Devices and Kits for Detecting the Novel Alcohol-specific Ethanol Glycoconjugate For convenience, the present invention can be provided as a kit comprising, in packaged combination, a holding container such as a vial or tube or cup or multi-welled plate, or the like, or an absorbent substrate for use with predetermined amounts of reagents and standards which can also be supplied.

One preferred kit is a test device comprising a strip or disk or piece, or the like, of TLC substrate or other suitable absorbent substrate to which body fluid (e.g. urine) is applied and then dried. For convenience, stability, and protection of the substrate and assays, the substrate may be supplied in or with a conveniently-sized housing or casing support means to further constitute the test device. In one aspect, a suitable amount of DAP reagent can be impregnated in the strip or the like. In another aspect, a pre-measured amount of DAP reagent can be supplied and applied to the absorbent substrate situated in the test device after contacting the strip or the like with sample. Alternatively, the absorbent substrate can be wet with the fluid test sample, the sample can be dried onto the absorbent substrate, and the absorbent substrate can be placed in a container with DAP reagent as provided. After a fluid sample is applied to the absorbent substrate, it is routinely dried prior to the addition of or contact with DAP reagent to elicit a colorimetric reaction. If the test sample (e.g. urine) contains alcohol-specific ethanol glycoconjugate as described herein, a blue color will typically develop after reaction of the DAP reagent and the alcohol-specific glycoconjugate.

In all cases, both positive and negative control samples can be supplied in the kit with the detection device or can be impregnated into the strip onto which the test sample is applied prior to reacting with the DAP reagent.

Another variant is a kit containing a pre-determined amount of the DAP reagent and individual, inert holding container (e.g. a tube or vial or multi-well plate or the like) into which the fluid test sample is placed. Such a kit may also comprise a carrier means being compartmentalized to receive in close confinement one or more holding containers such as vials, tubes, and the like, each of the containers comprising one of the separate elements to be used in the assay method. A pre-determined amount of a control sample can be optionally included in or provided with a separate container or in one of the containers included in the carrier means. The control sample can be a negative control such as a non-alcoholic, non-diabetic sample, or a positive control such as purified, alcohol-specific carbohydrates or a known, chronic alcoholic sample, or both. A specified amount of the test sample is placed in one holding container, and a suitable amount of DAP reagent is added to each control and test container. Alternatively, a pre-determined amount of DAP reagent can be supplied in the containers and a fluid test sample and control samples can be added to the separate containers.

Samples are incubated in the containers with the DAP reagent for a period of time sufficient to allow a calorimetric reaction to occur. Color will result from the reaction if the test sample contains the novel alcohol-specific carbohydrate. The positive control sample, but not the negative control sample, will calorimetrically react with the DAP reagent and both controls will serve to compare with the reaction in the test sample container. Particular components can be supplied in kit form for use in automated analyzers. The kit can also provide an independent test means for determining glucose associated with diabetes mellitus in the test sample or in another sample from the test individual.

Another aspect is a kit containing all materials necessary for the performance of ascending chromatography, including suitably-sized absorbent substrate (e.g. an aluminum-backed TLC plate), pre-mixed solvent mixture, or individual components of the solvent mixture to be combined and mixed prior to use, and a pre-determined amount of DAP reagent which can be supplied in a spray device, if desired. Alternatively, the individual components of the DAP reagent can be supplied and mixed together in the appropriate amounts prior to use. If desired, mixing and storage containers may be provided with the DAP reagent and solvent mixture components. A pre-determined amount of both negative and positive control samples may be included for application onto the substrate material prior to chromatographic development. Alternatively, the control samples can be pre-applied (i.e., impregnated) and dried onto the absorbent substrate material supplied in the kit. The materials contained in the kit can be used to run a chromatograph after application of test sample onto the substrate, and then to apply the DAP reagent to the developed and dried chromatograph to determine chronic alcoholism in the test sample.

It is contemplated that the test results obtained from the use of the kits in the form of the actual, used test device as a substrate strip, disk, plate, or the like, can be appropriately protected and stored for future interpretation or reference, and can be kept with an individual's records for a suitable period of time, if desired.

Other modifications for facility of performance of the test kit and its contents and of interpretation of test results are also envisioned.

EXAMPLES

The invention is further demonstrated by, but not limited to, the following illustrative examples:

Example I

Materials and Methods

Urine samples from alcoholics at different stages of rehabilitation were obtained through the VA Medical Center in Brooklyn, N. Y., and were kept frozen at −20° C. until analyzed. Urine from rats fed a liquid diet containing either 26% or 36% of their intake calories as alcohol, and pair-fed controls (which received no dietary alcohol) were obtained from Dr. Ananda Rao, VA Medical Center, Martinez, Calif. All solvents were obtained from Baker Laboratories and all chemicals were obtained from Sigma Chemical Company.

As described, the novel ethanol glycoconjugate was detected on thin layer chromatographs by spraying with diphenylamine-aniline-phosphoric acid reagent. Thin layer chromatography was carried out on silica gel G plates (Analtech, Newark, Del.) and chromatographed plates were developed in either a solvent mixture of chloroformmethanol-water in the proportions of 65:35:5, by volume, or chloroform-methanol-acetic acid water in the proportions of 50:20:6:1.5, by volume.

Example II

Simple Qualitative Assay for Chronic Alcohloism

This example describes a simple spot test for detecting the novel ethanol glycoconjugate specifically associated with chronic alcoholism in a sample.

A stock solution containing 2 g of diphenylamine, 2 ml of aniline, 15 ml of 85% orthophosphoric acid, and 80 ml of acetone (DAP reagent) was prepared according to the procedure as related in Zilic, Z., Blau, N., and Knob, M., (1979). *J. Chromatog.* 164:91–94). Reagents were of analytical grade or higher purity. The DAP reagent was preferably made up on the day of use. However, DAP reagent stock solution was also made up and stored in an appropriately-sealed container in the cold (e.g. 4° C.) for several weeks with no loss of stability or performance in these tests.

One drop (from about 2 µl to about 10 µl) of a non-concentrated urine sample was applied to an aluminium-backed silica gel G thin layer chromatography (TLC) plate or to a piece or strip cut from a larger TLC plate, and the urine spot was either air-dried or dried using a drying device, conveniently a hair blow-dryer set at cool to medium heat, or other suitable air-blowing device. One drop (about 5 µl to about 10 µl) of prepared DAP reagent was placed on the dried urine spot. The silica gel G thin layer chromatography plate or strip was covered with a clean glass plate and heated for approximately 30 minutes in an oven at 120° C., or in another suitable drying environment, for example, a microwave oven for about 60 to 90 seconds. As shown in FIG. 3, the spots containing an aliquot of urine sample from chronic alcoholics showed a dark blue, DAP-reactive coloration at the area of each of the urine spots, while the spots containing urine samples from normal, non-alcoholic, non-diabetic controls showed virtually no coloration in the regions where control urine was spotted and reacted with the DAP reagent. The slight background coloration evident in the control spots is expected due to nonspecific binding or reaction on the substrate; however, a clear difference can be observed between the control and test spot samples. The positive, intensely colored spots associated with chronic alcoholism were routinely well-defined and easily visualized in the spot assay. The spot assays, once performed and dried, could be saved or stored for future use or reference.

The spot assay is a rapid and reliable way in which to test or screen for the presence or absence of the novel ethyl glucuronide in individual urine samples. The convenience of the assay involves the ability to use only a small fraction of a test sample, which does not normally require further processing or concentration, to detect the ethyl glucuronide without a further separation step. This is due to the large quantity of the alcohol-specific ethyl glucuronide present and detectable in a small volume of an alcoholic's sample, relative to the undetectable and virtually nonexistent amounts of normal carbohydrates in an identical volume of unprocessed or nonconcentrated normal sample.

In the case of a non-normal, diabetic disease state, a spot of urine from a diabetic, non-alcoholic individual also showed an increased blue coloration when tested using the spot test method of the present invention because diabetics excrete large amounts of glucose in their urine, and glucose can be detected by the DAP reagent. However, diabetic, non-alcoholic individuals were readily distinguished from the long-term alcohol consumer by simultaneously testing the urine sample with "Clinistix"™, obtained from Miles, Inc., Diagnostic Division, Elkhart, Ind. "Clinistix"™ is a clinical test device in which absorbent material embedded with glucose oxidase is used to detect rapidly the presence of glucose in the urine of diabetics. "Clinistix"™ showed a positive reaction for diabetes, but was negative for chronic alcoholism, since glucose oxidase does not identify or detect the chronic alcohol-related carbohydrate of the present invention. Any commercially-available test or test device similar to "Clinistix"™ and used for routine analysis or determination of glucose present in the urine or blood of diabetics can be utilized when required to distinguish between a diabetic individual and a chronic alcoholic, when employing the subject methods. The results obtained using "Clinistix"™ or related test devices clearly indicated that glucose per se was not the alcohol-specific ethyl glucuronide linked to chronic alcoholism, and that an individual was a diabetic, independent of and apart from chronic alcohol consumption.

Example III
Chromatographic Assay for Chronic Alcoholism

The rapid test method for detecting the novel carbohydrate associated with chronic alcoholism was also performed by a qualitative and quantitative thin layer chromatography (TLC) procedure.

DAP reagent was prepared exactly as described in Example II and was placed in an appropriate container with a spray attachment. DAP reagent was stored in the dark in the sealed spray container for several weeks at 4° C. with no loss of stability or performance in these tests.

Spots of urine from chronic alcoholics, approximately 2 µl to 10 µl per spot, were applied to an aluminium-backed silica gel G TLC plate or piece or strip cut from a larger TLC plate. Replicate samples were frequently run on the same TLC plate. Although other types of TLC plates may be used, aluminium-backed silica gel G plates were easy to use and yielded an optimal separation of alcohol-specific carbohydrates and standard carbohydrates. All of the samples to be assayed were well-spaced both from each other (typically on the order of 1 cm apart on the TLC plate) and from the bottom and side edges of the chromatography plate (approximately 1 cm to 3 cm from the edges of the TLC plate). Samples were developed chromatographically in a solvent system which was a mixture of chloroform/methanol/water in the proportions of 65:35:5, by volume. Chromatography development was performed in a vapor-saturated chromatography chamber at room temperature. For optimal resolution, TLC running time was approximately 30 minutes and the migration distance of the solvent mixture was approximately 15.5 cm, preferably from about 10 cm to about 20 cm, from the sample application line. After developing, the TLC chromatograph was air-dried and the surface of the chromatography plate was sprayed and wet evenly with DAP solution. The sprayed TLC plate was air-dried briefly, covered with a clean glass plate, and heated in a 120° C. oven, for about 10 to 20 minutes. After incubation with DAP reagent, well-defined, non-diffuse, dark blue spots at an $R_f$ value of about 0.2 to about 0.3 on the TLC chromatograph indicated chronic alcoholism. Urine samples from diabetics showed dark blue spots (identified as glucose) which migrated at an $R_f$ value of about 0.4 and which were clearly distinct from the migration distance and the $R_f$ of about 0.3 of the spot produced by the alcohol-specific glycoconjugate in the urine of a chronic alcoholic. For confirmation, the diabetic samples were independantly tested using "Clinistix"™ or a similar diabetes glucose-detection device.

Figure 4A:
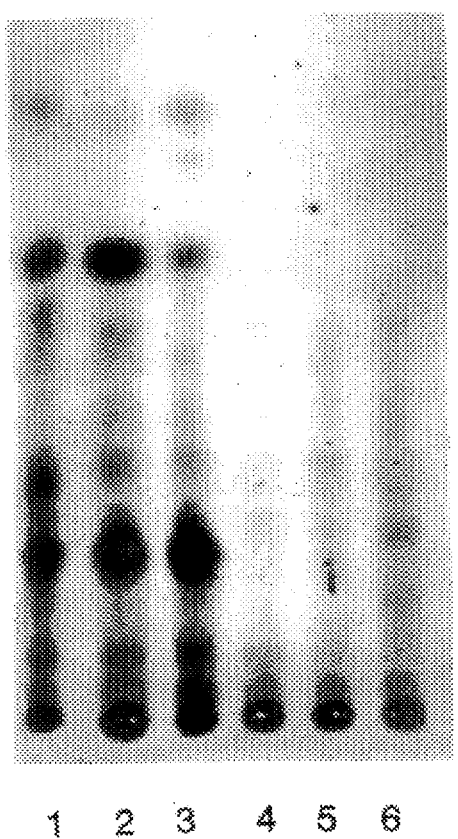
FIGS. 4A and 4B show a thin layer chromatograph treated with DAP reagent and containing urine samples from chronic alcoholics within a week after their last drink (Lanes 1–3) and urine samples from normal, non-alcoholic controls (Lanes 4–6).
Figure 4B:
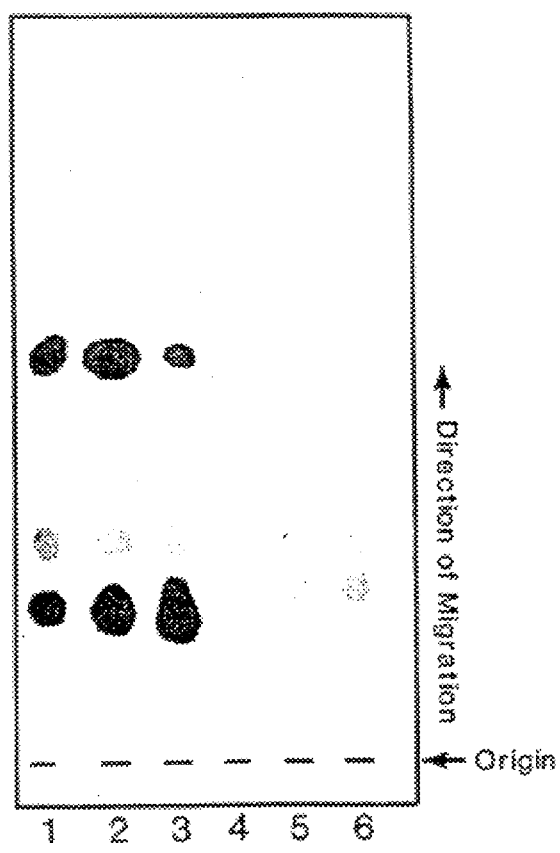

As shown in FIG. 4, urine samples from three chronic alcoholic subjects, within a week after their last drink, were run in parallel on the same TLC plate with urine samples from three normal, non-alcoholics which served as negative controls. The intense, dark spots at $R_f$ values between approximately 0.17 to approximately 0.25 were seen in all three lanes containing urine from the chronic alcoholics (Lanes 1–3), but were not seen in any of the control lanes containing urine from non-alcoholics (Lanes 4–6). The most abundant and reproducible spots indicating the presence of the novel alcoholspecific glycoconjugate were routinely observed at an $R_f$ value between about 0.15 to about 0.3. The faster-migrating DAP-reactive compounds were variable and were not detected in all chronic alcoholics. Negative control samples reproducibly showed neither the alcohol-specific glycoconjugate nor the faster-migrating compounds using the present assay.

The levels of the alcohol-specific glycoconjugate visualized after exposure to DAP reagent may be estimated by scanning the positively colored spots on the plates in a densitometric spectrophotometer as reflected in TABLE 4. TABLE 4 reveals the quantitative aspect of monitoring an alcoholic condition by the TLC method of the present invention. The alcohol-specific ethyl glucuronide carbohydrate was monitored in urine samples from individual subjects at various times after their last drink in accordance with the invention. Subjects were from the alcohol detoxification unit of a Veteran's Association Medical Center. Urine samples from chronic alcohol users were subjected to TLC analysis 0–7 days after their last drink, 8–14 days after their last drink, and more than 14 days after their last drink. Each column in TABLE 4 lists discrete values which represent different individual patient samples. The numbers shown in each column represent the amounts of alcohol-related ethyl glucuronide found in different patients who were tested for the presence of the novel carbohydrate after having had their last drink in the time period specified at the top of each column. The mean values, beneath each column (in bold-faced type) and shown for each period of alcohol consumption, represent the trend in detecting the presence of the alcohol-specific glycoconjugate in different patients who were tested as specified in the table headings. For example, in column 1, at "0–7 Days" after their last drink, 21 individual subjects were analyzed and the mean value of carbohydrates determined from this group of individuals is shown as "30.80+/–19.24". In column 2, at "8–14 Days" after their last drink", samples from 18 individual subjects, not necessarily those tested in column 1, were analyzed and the mean value of carbohydrates determined from this group is shown at the bottom of column 2 as "5.29+/–4.37", a value strikingly lower than that for individuals who had been tested for the presence of alcohol at 0–7 days after their last drink. Similarly, in column 3, at "greater than 14 Days" after their last drink, 11 different subjects were analyzed for the presence of alcohol-related carbohydrates, and the mean value found at this time was "4.23+/–3.00", a value that is still lower than that found in individuals tested at 8–14 days after their last drink. Because the mean values of the novel alcohol-specific ethanol glycoconjugate found for each of the different patients in the time periods tested are shown at the bottom of each column, the mean values are to be compared, rather than the individual numbers between the columns. Urine from twenty social drinkers failed to show detectable levels of the ethanol glycoconjugate.

To obtain the data in TABLE 4, the TLC chromatographs were analyzed by densitometry after reaction with the DAP reagent and visualization of the colored spots. The colored spots of the ethanol glycoconjugate were quantified by the densitometric analysis of the thin layer chromatographs. Many urine samples were tested for each time category, and the mean values and standard deviations (+/–SD) were determined. The results shown in TABLE 4 indicate that high levels of the alcohol-specific ethanol glycoconjugate were detected in urine from individuals tested up to seven days after alcoholic drinking was terminated, and that the levels of the glycoconjugate significantly decreased in urine the longer that an individual had abstained from steady alcohol consumption.

TABLE 4

Levels of alcohol-specific glycoconjugate detected in urine (µg/mg urine creatinine)
Days after last drink

| 0–7 Days | 8–14 Days | >14 Days |
| --- | --- | --- |
| 31.61 | 12.41 | 4.40 |
| 31.40 | 10.62 | 4.61 |
| 66.49 | 2.76 | 1.53 |
| 17.47 | 2.04 | 0.96 |
| 10.31 | 0.24 | 4.76 |
| 68.36 | 1.45 | 2.61 |
| 14.09 | 4.89 | 6.20 |
| 31.99 | 13.18 | 6.23 |
| 36.03 | 2.23 | 3.21 |
| 73.45 | 11.71 | 11.19 |
| 36.80 | 8.43 | 0.79 |
| 33.14 | 2.42 | |
| 10.29 | 3.78 | |
| 13.25 | 0.15 | |
| 14.28 | 7.19 | |

TABLE 4-continued

Levels of alcohol-specific glycoconjugate detected in urine (µg/mg urine creatinine)
Days after last drink

| | 0–7 Days | 8–14 Days | >14 Days |
| --- | --- | --- | --- |
| | 11.71 | 1.03 | |
| | 34.58 | 7.21 | |
| | 33.40 | 3.57 | |
| | 41.03 | | |
| | 27.45 | | |
| | 9.54 | | |
| MEAN +/– SD | 30.80 +/– 19.24 | 5.29 +/– 4.37 | 4.23 +/– 3.00 |

Alcohol-specific carbohydrates were quantified by densitometric analysis of thin layer chromatograhs after reacting with diphenylamine/aniline/phosphoric acid reagent and visualizing colored spots. The values were normalized to urinary creatinine concentration and are expressed as µg/mg creatinine using glucose as a standard.

If the test TLC chromatographs cannot be scanned for quantification immediately, they may be stored in the dark at 4° C., usually wrapped in aluminum foil, for several weeks, months, and even for some years after development and drying, and prior to densitometric analysis.

Figure 5A:
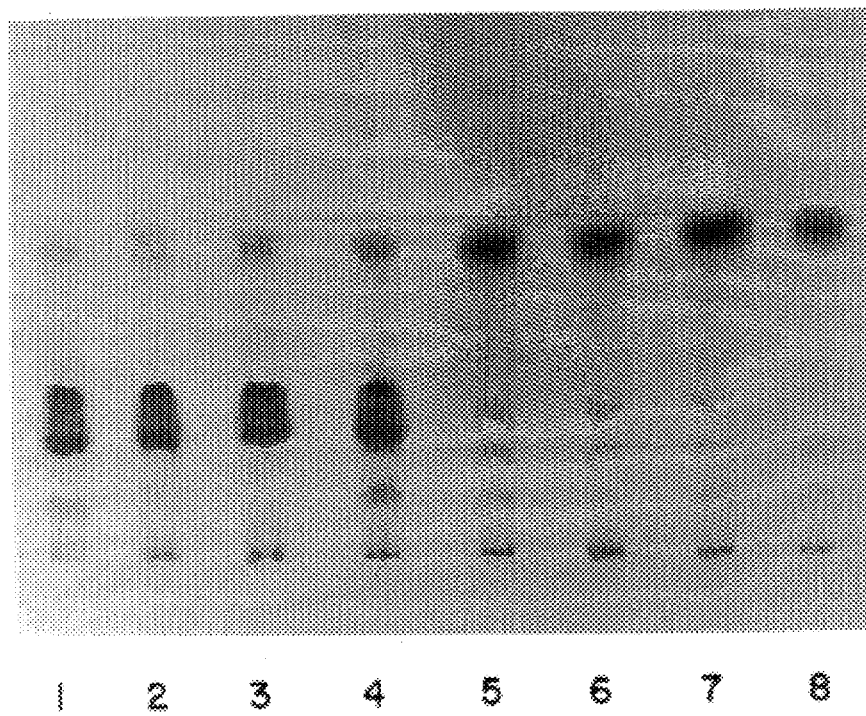
FIGS. 5A and 5B show a DAP reagent-treated thin layer chromatograph of urine samples from rats fed 36% alcohol-derived calories for two weeks, with Lanes 1–4 showing urine samples from the experimental, alcohol-fed animals and lanes 5–8 showing urine samples from control, non-alcohol consuming animals. The TLC was performed on silica gel G plates in a chloroform/methanol/acetic acid/water solvent system, mixed in the proportions of 50:20:6:1.5, by volume, and DAP reagent was sprayed onto the dried chromatograph after the TLC was run. The alcohol-specific ethanol glycoconjugate, apparent only in lanes 1–4, migrated about 3 cm to about 4 cm from the origin.
Figure 5B:
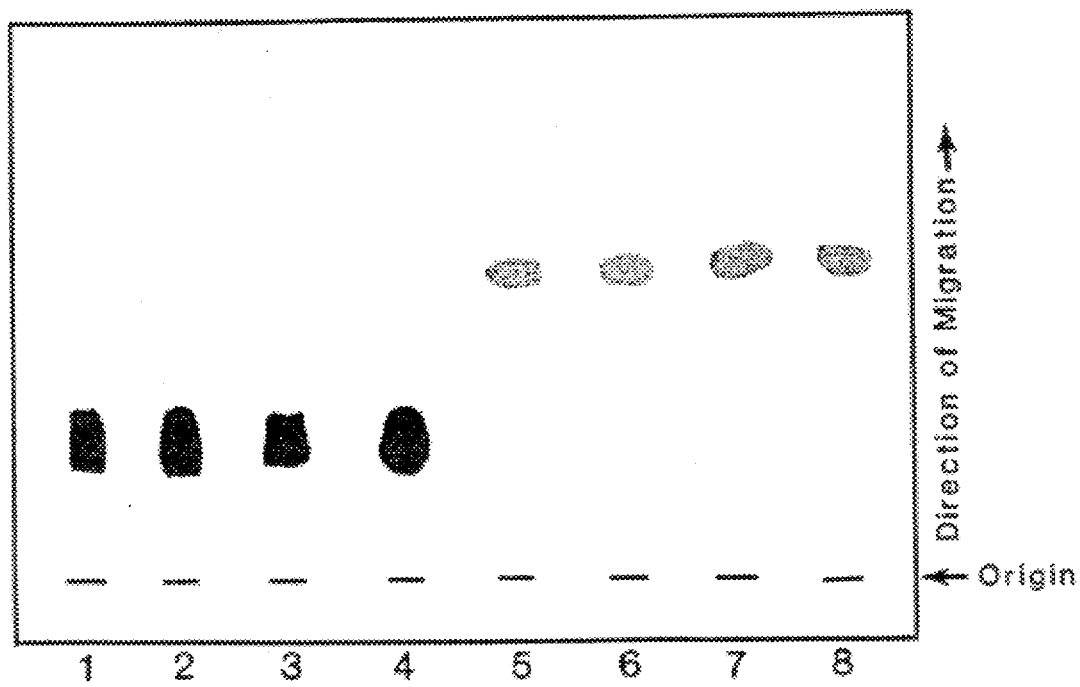

Example IV
Human and Non-human Animal Models and Tissue Testing for Detecting or Monitoring Chronic Alcoholism Experiments using rats maintained on a controlled liquid diet in which 36% of the calories were obtained from alcohol confirmed that alcohol-specific ethanol glycoconjugate was excreted in the urine of animals fed on this regimen for two to four weeks. FIG. 5 demonstrates that a 10 µl spot of urine from four rats maintained on the alcohol diet for two weeks (Lanes 1–4) showed a distinct blue region of color after chromatography in the chloroform/methanol/acetic acid/water mixed solvent and after reaction with DAP reagent. The alcohol-specific glycoconjugate was determined to have $R_f$ values of between 0.17 to about 0.27. Control animals, which had not been maintained on the alcohol diet (Lanes 5–8), showed no densely colored spots at a migration distance corresponding to the spots which indicated long-term alcohol consumption, as observed in the test animals.

The non-specific DAP-reactive component having an $R_f$ value of about 0.49 and seen in all samples is believed to be a metabolite of dietary carbohydrate. The test rats used in these experiments were fed an isocaloric diet in which ethanol was substituted for the dextrin-maltose carbohydrate which was fed to the normal control rats so that the controls received higher levels of carbohydrate. Such fast-migrating compounds were not detected in samples from human controls. In the same solvent mixture, the alcoholspecific glycoconjugate detected in rats and in humans have virtually identical $R_f$ values. Typically, the levels of the novel alcohol-specific glycoconjugate are several times higher than the levels of the fast-migrating compounds, and both are readily distinguishable. The alcohol-specific carbohydrates also have $R_f$ values less than that of glucose.

In addition, rats fed for two weeks on a diet in which 26% of their calories was alcohol produced appreciable amounts of the novel glycoconjugate in their urine. The amount of the glycoconjugate quantified in the urine depended upon both the dietary level and the duration of alcohol intake in the test animals.

Figure 6:
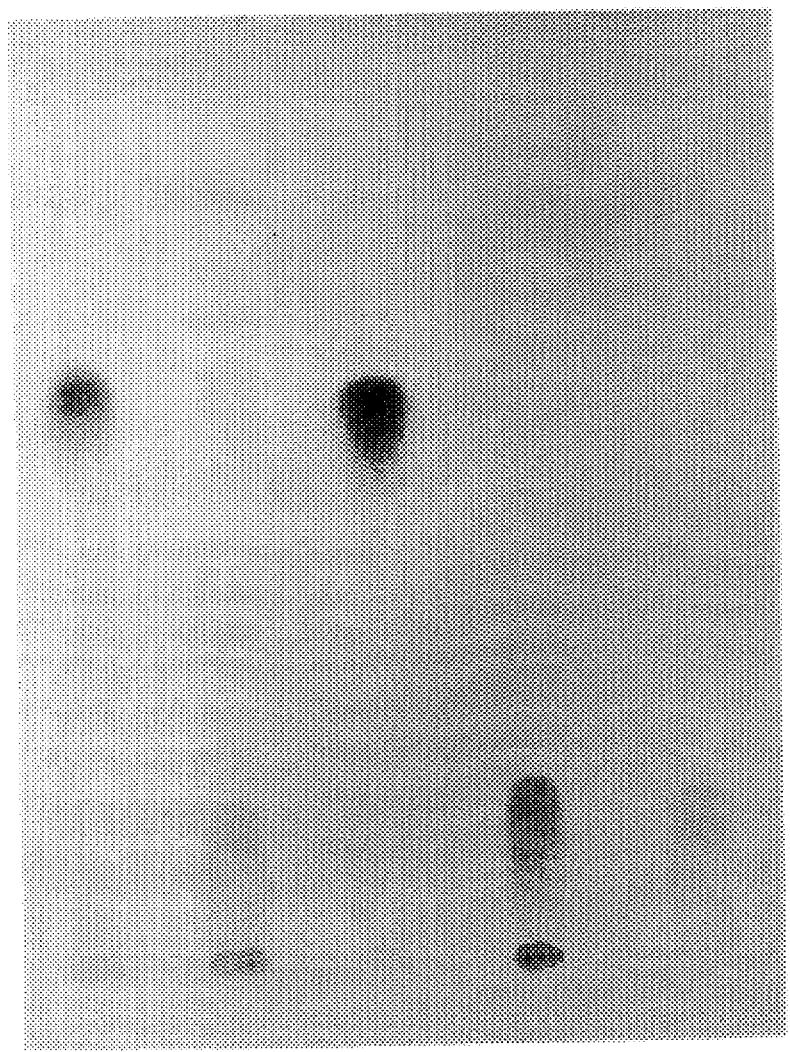
FIG. 6 is a thin layer chromatograph of the novel alcohol-specific ethanol glycoconjugate upon treatment with β-glucuronidase as described in Example VII. Lane 1: isolated ethanol glycoconjugate from alcohol-fed rats; lane 2: alcohol-specific glycoconjugate isolated from rat urine and treated with β-glucuronidase yielding glucuronic acid; lane 3: alcohol-specific ethanol glycoconjugate isolated from urine of a chronic alcoholic; lane 4: alcohol-specific glycoconjugate isolated from chronic alocholic urine and treated with β-glucuronidase yielding glucuronic acid; lane 5: glucuronic acid control.

Thin layer chromatographic analysis of the glycoconjugate from urine of chronic alcoholics also clearly shows excretion of ethyl glucuronide with the same thin layer chromatographic mobility as that detected in rats fed alcohol (FIG. 6).

Autopsied liver samples prepared from humans who had been chronic alcoholics were evaluated in both the spot test and the TLC test of the present invention. The liver samples tested showed the presence of the alcohol-specific ethyl glucuronide virtually identical to the carbohydrates seen in living chronic alcoholics and in alcohol-fed rats. Thus, the present invention shows utility for postmortem examination, detection, and discovery of chronic alcoholism.

In a double-blind controlled study, it was found that chronic alcoholic human beings who were kept on an alcohol-free diet for at least two weeks showed no signs of the chronic alcohol-specific ethyl glucuronide when their urine was tested in the spot or TLC assays described herein. Thus, the present invention shows utility not only for detecting chronic alcoholism, but also for generally monitoring the status of the alcoholic condition, especially during treatment or rehabilitation.

Example V
PURIFICATION AND ISOLATION OF THE NOVEL ETHANOL GLYCOCONJUGATE

The novel ethanol glycoconjugate was purified and isolated from urine by thin layer chromatography. After centrifugation at 1,000×g for 5 minutes, urine supernatant was spotted on prewashed and scored silica gel G thin layer plates and developed in a solvent mixture of chloroform-methanol-water in the proportions of 65:35:5, by volume. A portion of the plate was separated, sprayed with diphenylamine-aniline-phosphoric acid reagent, and the glycoconjugate was visualized by heating the chromatograph at 120° C. for 10 to 20 minutes. The area corresponding to the glycoconjugate, which was well-separated from the origin and accessible on the plate, was scraped and eluted with a methanol and water mixture in the proportions of 50:50, by volume.

Figure 7A:
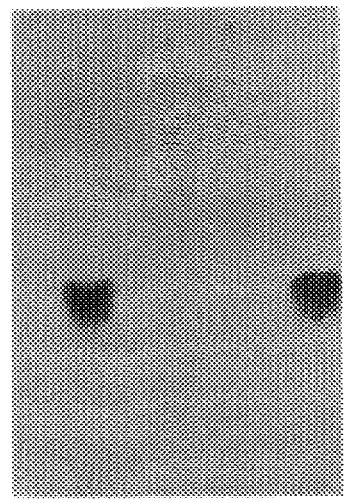
FIGS. 7A and 7B show a thin layer chromatograph demonstrating that the alcoholspecific ethyl glucuronide biomarker isolated as described from a urine sample of a chronic alcoholic is not dolichol or dolichol-related. The samples run in lanes 1–3 of both
Figure 7B:
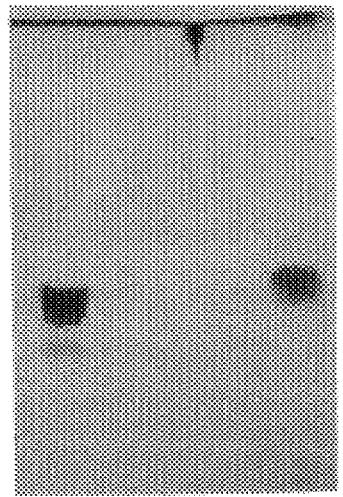

The purified material was subjected to further thin layer chromatography on a silica gel G plate with a developing solvent mixture comprised of chloroform-methanol-acetic acid-water in the proportions of 50:20:6:1.5, by volume. For a last isolation step, the final product was eluted from the TLC spot as described, filtered through a 0.25 μ filter (Millipore), and dried under a stream of nitrogen. The isolated glycoconjugate product was observed as a single spot on thin layer chromatography in both solvent systems as described above, and was detected as a single spot by spraying with diphenylamine-aniline-phosphoric acid reagent or by charring (FIGS. 7A and 7B).

Example VI
Characterization of the Novel Ethyl Glucuronide Following Phenacyl Ester Derivative Preparation and High Performance Liquid Chromatography (HPLC)

Phenacyl derivatives of the urine samples from alcohol-fed rats (36% of their calories was alcohol over 2–4 weeks) and pair-fed control rats which had received no alcohol were prepared essentially by the method described by E. Mentasti et al., (1985), "Derivatization, identification, and separation of carboxylic acids in wines and beverages by high performance liquid chromatography", *J. Chromatog.*, 322:177–189. Briefly, 5 μl of the urine sample was treated with 7.5 μl of phenacylbromide (0.17M) in acetone and 7.5 μl of 18-crown-6 (0.017M) in acetone at 80° C. for 30 minutes. The solvent was evaporated and the sample was reconstituted in 200 μl of methanol. An aliquot of sample equivalent to 0.25 μl of urine was injected into an HPLC system with the following parameters: HPLC column: Reversed phase C-18 (0.4×10 cm). Solvent: water-methanol (65:35, v/v) at 1 ml per minute. Detector: Ultraviolet set at 254 nm. As depicted in FIGS. 8A and 8B, the spectrum of the sample derived from rats fed a diet containing 36% of the calories from alcohol (8A) showed a large and distinct peak which eluted at about 10 minutes. In contrast, no such peak was evident in sample derived from control rats which had not been fed with alcohol (8B). Ethyl glucuronide phenacyl ester had a retention time on HPLC of 10.8 minutes.

Example VII
Isolation and Characterization of 1-O-Ethyl Glucuronic Acid by Hydrolysis of the Isolated Ethyl Glucuronide The ethyl glucuronide was isolated as described in Example V, and was treated with 100 units of β-glucuronidase (Sigma Chemical Company) in 0.1M sodium acetate buffer, pH 5, at 37° C. Within four hours, ethyl glucuronide was hydrolyzed and produced a product having a mobility of 1-O-ethyl glucuronic acid as determined by thin layer chromatography. Specifically, β-glucuronidase treatment of the isolated glycoconjugate from alcohol-fed animals (i.e., rats) and from chronic alcoholics released ethyl glucuronic acid (FIG. 6) indicating that the main component of the ethanol glycoconjugate is ethyl β-glucuronide with an alcohol in the 1-position, since β-glucuronidase does not hydrolyze acylglucuronides.

Acid hydrolysis of 1-O-ethyl glucuronide in 1 N HCl at 80° C. for fifteen hours produced both glucuronic acid and glucuronic acid lactone as a secondary biproduct of the hydrolysis reaction.

Since ethyl glucuronide is produced in direct response to alcohol in the diet, the excretion of this novel carbohydrate as a detoxification product seems reasonable. To verify the structure of the isolated alcohol-specific carbohydrate as 1-O-ethyl glucuronic acid, 1-O-ethyl glucuronic acid was chemically synthesized as described in Example VIII and confirmatory tests were performed.

Figure 9A:
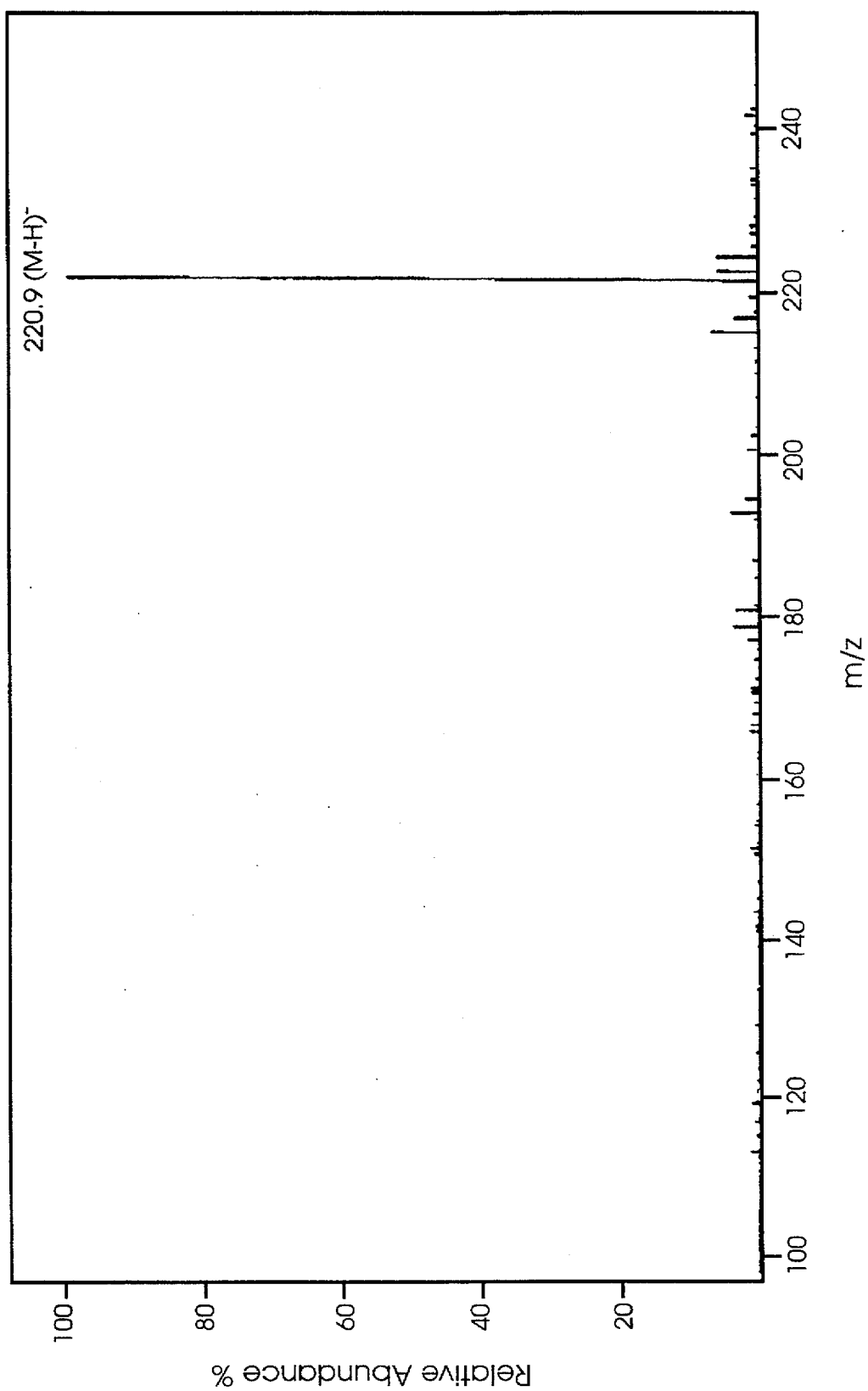
FIG. 9A is a negative ion mass spectrum of the novel alcohol-specific carbohydrate isolated from the urine of rats fed a diet comprising alcohol. The molecular ion mass of 220.9 corroborates the structure of ethyl glucuronide.
Figure 9B:
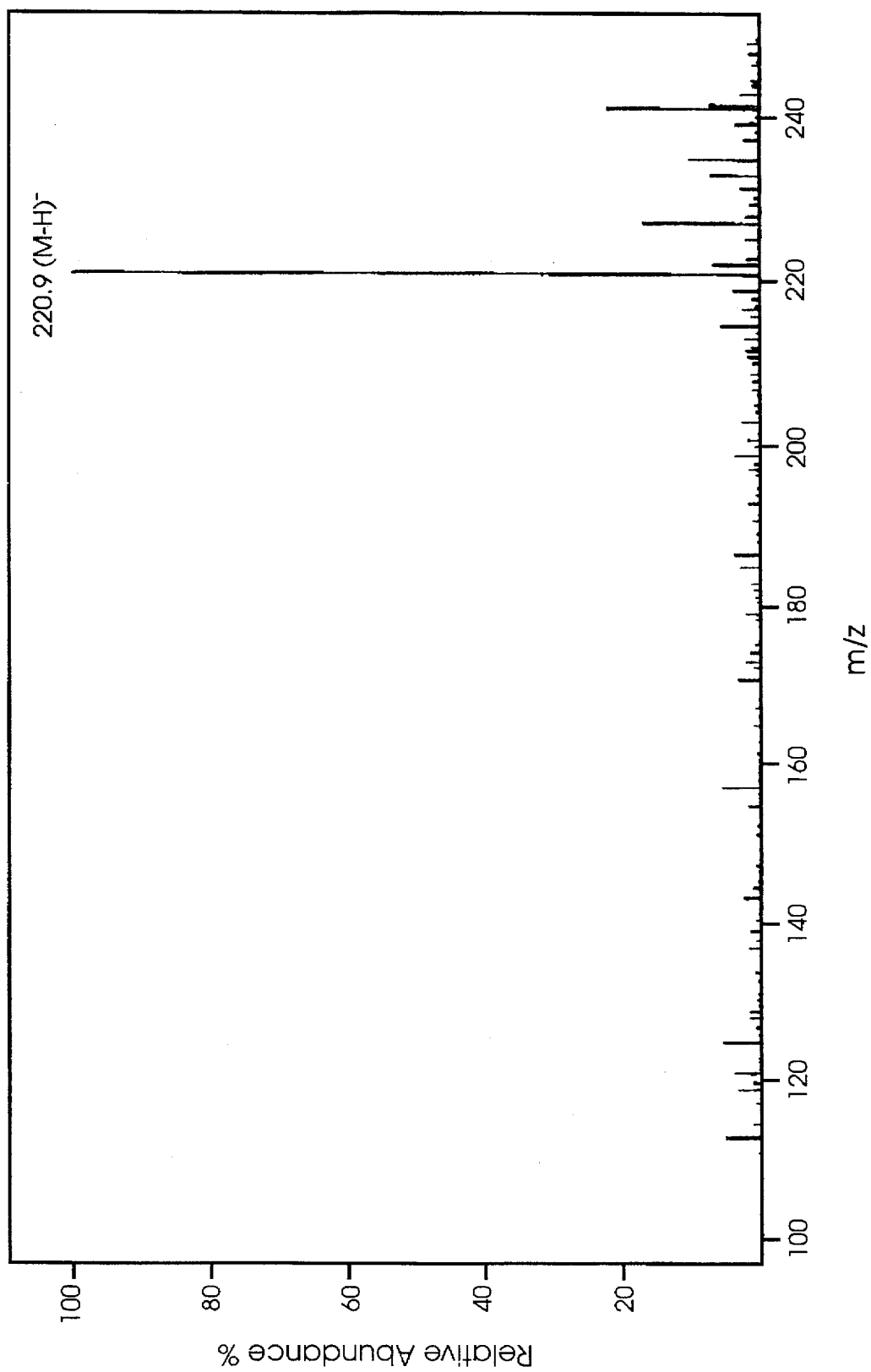
FIG. 9B is a negative ion mass spectrum of the novel alcohol-specific carbohydrate isolated from urine samples of alcoholic individuals. The molecular ion mass of 220.9 corroborates the structure of ethyl glucuronide.

Mass spectroscopic analysis of the alcohol-specific glycoconjugate isolated from the urine of rats fed alcohol and from the urine of chronic alcoholics was carried out at the Rockefeller University Mass Spectroscopic Laboratory by the electrospray method. Electrospray was done in a solution of 10% isopropanol at 1,200 v at a rate of 4 μl/min. In addition, mass spectroscopy was simultaneously carried out on chemically-synthesized 1-O-ethyl glucuronic acid as a control. The mass spectroscopic analysis of all three products testsed gave a molecular ion mass (M-H) at m/z of 220.9 (FIGS. 9A and 9B). The expected molecular weight of 1-O-ethyl glucuronic acid is 222.

Figure 10:
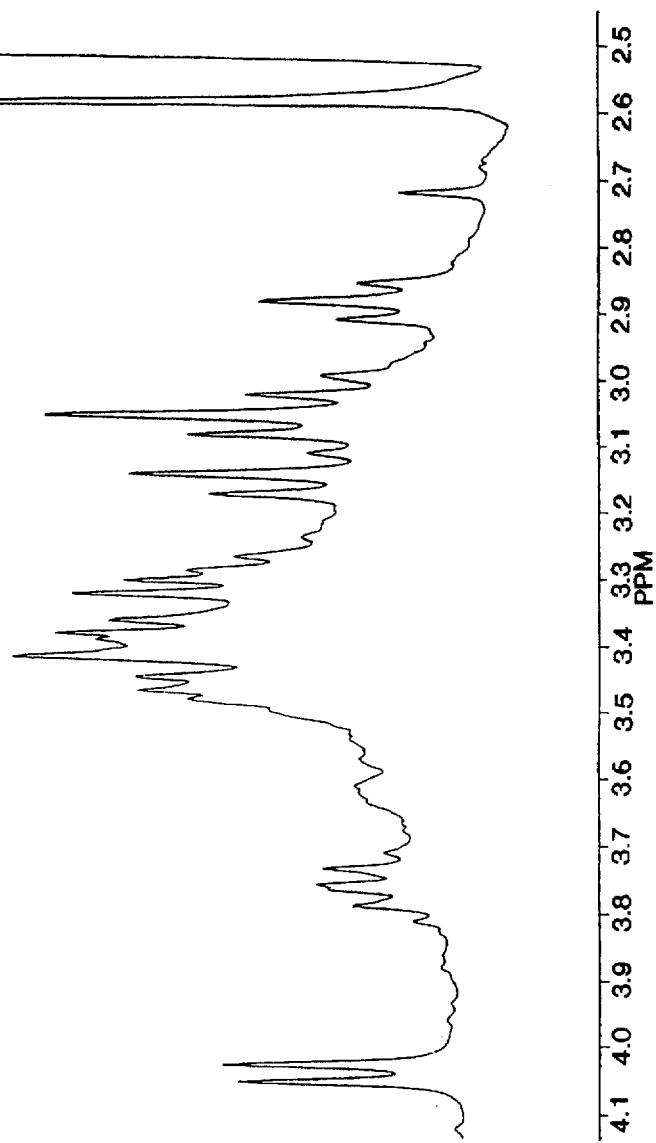
FIG. 10 shows a spectrum resulting from NMR analysis of the novel ethyl glucuronide as described in Example VII.

Proton nuclear magnetic resonance spectra were recorded at 300 MHz in deuterated DMSOOd6 with a Bruker instrument (FIG. 10).

Example VIII
Chemical Synthesis of 1-O-Ethyl Glucuronic Acid

Methyl (2,3,4-triacetyl-1-bromo-1-deoxy-D-glucopyran) urinate was synthesized according to the procedure of Bollenback et al. (1955), "The synthesis of aryl-Dglucopyranosiduronic acids", *J. Am. Chem. Soc.*, 77:3310–3315. In brief, glucurono-63-lactone (Sigma Chemical Company) was converted into methyl glucopyranuronate by stirring a methanolic suspension with sodium methylate. The methyl ester was acetylated with acetic anhydride in pyridine in the presence of perchloric acid. The resulting crystalline methyl [1,2,3,4-tetraacetylglucopyran] urinate was brominated with 335 HBr in acetic acid to give crystalline methyl (tri acetyl-1-bromoglucopyran) urinate. Absolute ethyl alcohol (1.5 g) was mixed with the bromo sugar (1.2 g) and silver carbonate (1 g) in benzene and stirred magnetically at room temperature overnight. The mixture was filtered and the residue was washed with benzene. The clear solution was evaporated to dryness in a rotary evaporator. Further drying in a desiccator over calcium chloride yielded a crystalline product melting at 142° C. to 143° C. The product was hydrolyzed by treating with 0.5M sodium hydroxide at room temperature and neutralized with glacial acetic acid. The synthetic 1-O-ethyl-glucuronic acid had the identical thin layer chromatographic behavior as the alcohol-specific glycoconjugate component isolated either from rats fed a high level of alcohol or from chronic alcoholics.

Example IX

The Novel Ethanol Glycoconjugate is not Dolichol and is not Related to Dolichol

Experiments were performed to demonstrate the distinct nature of the novel glycoconjugate and its major ethyl glucuronide component. One such analysis showed that dolichol is not detected by the methods used to detect chronic alcoholism as described and that dolichol is not related to the novel alcohol-specific carbohydrate discovered by the inventors and detected by the disclosed assays. Thin layer chromatography was carried out as described and shown in FIGS. 7A and 7B. FIG. 7A shows the results of spotting 10 μg of the isolated alcohol-specific component from alcoholic urine samples in lane 1, 10 μg of dolichol in lane 2, and 10 μg of chemically-synthesized 1-O-ethyl glucuronide in lane 3 on silica gel G, developing the TLC in a solvent mixture of chloroform-methanol-acetic acid-water, in the proportions of 50:20:6:1.5, by volume, and then spraying with DAP reagent. Dolichol spotted in lane 2 does not react with the DAP reagent, unlike the novel ethanol glycoconjugate carbohydrate biomarker in lane 1 and the chemically-synthesized control in lane 3. FIG. 7B shows the results of the same TLC as described in FIG. 7A, except that instead of reacting with DAP reagent, the TLC plate was sprayed with 0.6% potassium dichromate in sulfuric acid and charred by heating at 180° C. for 1 hour. Charring showed the novel ethyl glucuronide in lane 1, the chemically-synthesized 1-O-ethyl glucuronide in lane 3, as well as the presence of dolichol in lane 2 as the spot at the very top of the TLC chromatograph at the solvent front. These results demonstrated that dolichol is not detected by DAP reagent and confirms the unique nature of the ethanol glycoconjugate.

The references disclosed in the specification are incorporated by reference in their entirety.

Although the foregoing invention has been described in some detail by way of illustration and example for purposes of clarity of understanding, it will be obvious to those skilled in the art that certain changes and modifications may be practiced without departing from the spirit and scope thereof, as described in the specification and defined in the appended claims.

What is claimed is:

1. An assay method for diagnosing chronic alcoholism in a person being tested for alcoholism, comprising the steps of:
   (a) obtaining a body fluid sample from the person being tested; said sample obtained at least 7 days after the person has terminated alcohol consumption;
   (b) reacting an aliquot of the test sample with a reagent comprising diphenylamine, aniline, and phosphoric acid, or DAP reagent;
   (c) comparing the resulting colorimetric reaction of the DAP reagent in the test person's sample with a control sample from a person who is non-alcoholic and non-diabetic such that a color in the test sample relative to the control sample indicates that:
      i) ethyl β-glucuronide is present in the test person's sample, said ethyl β-glucuronide being a diagnostic biomarker of chronic alcoholism; and said ethyl β-glucuronide being detectable in the person's sample at least 7 days after the person has terminated the consumption of alcohol; and
      ii) the person being tested is a chronic alcoholic.

2. The method of claim 1, wherein in step (a) the body fluid sample is a urine sample.

3. The method of claim 2, wherein the urine sample is not concentrated.

4. The method of claim 1, further comprising the step of:
   (d) assaying a second aliquot from the test sample to independently identify diabetes-associated glucose in the test person.

5. The method of claim 1, wherein the body fluid sample is selected from the group consisting of blood, serum, plasma, saliva, amniotic fluid, and body tissue fluid preparation.

6. The method according to claim 1, wherein the samples are applied as spots and dried onto an absorbent substrate prior to step (b).

7. The method of claim 6, wherein the absorbent substrate is a thin layer chromatography plate coated on its surface with silica gel G.

8. The method of claim 7, wherein the control and test samples are urine samples; wherein from about 2 μl to about 50 μl of the urine is spotted onto the plate, the spotted substrate is dried; and wherein DAP reagent is wettably contacted with the dried spotted substrate, and the plate is dried.

9. The method of claim 1, further comprising:
   (d) providing a positive control of a sample from a chronic alcoholic, said sample known to contain alcohol-specific ethyl glucuronide, or a chemically synthesized ethyl glucuronide; and
   (e) comparing the resulting calorimetric reaction of the DAP reagent in the test person's sample with the colorimetric reaction in the control sample, with a color in the test sample and in the control sample of step (d) being indicative of the presence of ethyl β-glucuronide as a diagnostic biomarker of chronic alcoholism.

10. An assay method for diagnosing chronic alcoholism, comprising the steps of:
   (a) obtaining a control sample from a non-alcoholic and non-diabetic person;
   (b) obtaining a test sample from a person being tested for chronic alcoholism, wherein the test sample is obtained at least 7 days after the person has terminated the consumption of alcohol;
   (c) subjecting an aliquot of the control sample and an aliquot of the test sample to ascending chromatography on absorbent substrate in a water-containing organic solvent mixture suitable for separating components contained in the samples; wherein the solvent mixture is not comprised of acetone, chloroform, and water in the proportions of 85:10:5, by volume;
   (d) adding a reagent comprising diphenylamine, aniline, and phosphoric acid, or DAP reagent to the chromatogram, wherein the DAP reagent can colorimetrically react with the carbohydrates associated with chronic alcoholism in the samples; and
   (e) comparing the results of the colorimetric reactions in the control and test samples such that the presence of colored spots from the test sample at positions on the substrate different from those of the control indicates a reaction of the DAP reagent with ethyl glucuronide, said glucuronide being detectable at least to 7 days after the person has terminated alcohol consumption, and reliably diagnosing chronic alcoholism in the person.

11. The assay method of claim 10, further comprising the step of testing a second sample from the test person to independently identify diabetes-associated glucose in the test person.

12. The assay method of claim 11, wherein the fluid samples to be assayed are body fluids selected from the group consisting of blood, serum, plasma, saliva, amniotic fluid, urine, and body tissue fluid preparation.

13. The assay method of claim 12, wherein the fluid sample is urine.

14. The assay method of claim 13, wherein the urine sample is not concentrated.

15. The assay method of claim 10, claim 13 or claim 14, wherein the solvent mixture used in step (c) is comprised of chloroform, methanol, and water in the proportions of 65:35:5, by volume, or chloroform, methanol, acetic acid, and water in the proportions of 50:20:6:1.5, by volume.

16. The assay method of claim 15, wherein the ascending chromatography is carried out in a chamber saturated with vapors from the solvent mixture.

17. The assay method of claim 15, further comprising the step of quantitatively determining the amount of the DAP reagent reactive with said samples of step (d) on the chromatograph substrate using spectrophotometric densitometry analysis.

18. The assay method of claim 17, wherein the samples are applied as spots onto an absorbent substrate prior to step (c).

19. The assay method of claim 18, wherein the absorbent substrate is an aluminum-backed thin layer chromatography plate coated with silica gel G on its surface.

20. The assay method of claim 19, wherein the test sample is a urine sample; wherein a small amount of the urine is spotted onto the chromatography plate and the spotted chromatography plate is dried; wherein the chromatography plate is developed in a solvent mixture comprised of chloroform, methanol, and water in the proportions of 65:35:5, by volume, or in a solvent mixture comprising chloroform, methanol, acetic acid, and water in the proportions of 50:20:6:1.5, by volume, until the solvent front has moved a suitable distance away from the sample spot, and the developed chromatography plate is dried; and wherein DAP reagent is applied to the developed chromatography plate and the chromatography plate is dried.

21. A kit for diagnosing chronic alcoholism by determining the presence of ethyl β-glucuronide as a biomarker of chronic alcoholism in body fluid samples from individuals being tested for chronic alcoholism, which comprises an absorbent substrate capable of retaining an aliquot of the sample to be tested, the absorbent substrate being impregnated with a reagent comprising diphenylamine, aniline, and phosphoric acid or DAP reagent; wherein, on the absorbent substrate the test sample is applied and dried; and wherein, on the absorbent substrate the impregnated DAP reagent has the capability of colorimetrically reacting with the ethyl β-glucuronide in the test sample if the sample contains said ethyl glucuronide, wherein the presence of ethyl glucuronide is indicative of chronic alcohol consumption; and further comprising a positive control sample containing ethyl glucuronide from a chronic alcoholic or chemically synthesized ethyl glucuronide as a positive control, a negative control sample from a non-alcoholic, non-diabetic individual, and a means to identify diabetes-associated glucose in the test sample; the samples applied to or impregnated in the absorbent substrate, with the DAP reagent on the absorbent substrate colorimetrically reacting with ethyl glucuronide in the positive control sample on the substrate, but not colorimetrically reacting with the negative control sample.

22. The kit according to claim 21, wherein the absorbent substrate is a strip.

23. A method of isolating ethyl glucuronide as a biomarker specifically associated with the diagnosis of chronic alcohol consumption, comprising the steps of:

(a) obtaining a fluid sample containing the chronic alcohol-specific ethyl glucuronide, wherein the fluid sample is obtained at least 7 days after an individual has terminated the consumption of alcohol;

(b) subjecting the sample to ascending chromatography on an absorbent substrate material using a solvent mixture capable of resolving the ethyl glucuronide away from the origin; wherein the solvent mixture is not comprised of acetone, chloroform, and water in the proportions of 85:10:5, by volume;

(c) colorimetrically reacting the ethyl glucuronide on the chromatograph with a reagent comprising diphenylamine, aniline, and phosphoric acid, or DAP reagent; and (d) extracting the ethyl glucuronide from the chromatograph with a water-containing organic solvent mixture; wherein the solvent mixture is not comprised of aectone, chloroform and water in the proportions of 85:10:5, by volume.

24. The method of claim 23, wherein the fluid sample of step (a) is a urine sample.

25. A method of isolating hydrolysis products of ethyl glucuronide specifically associated with chronic alcohol consumption and a diagnostic biomarker of chronic alcohol consumption, comprising the steps of:

(a) obtaining a fluid sample containing the chronic alcohol-specific ethyl glucuronide, wherein the fluid sample is obtained at least 7 days after an individual has terminated the consumption of alcohol;

(b) subjecting the sample to ascending chromatography on an absorbent substrate material using a solvent mixture capable of resolving the ethyl glucuronide away from the origin; wherein the solvent mixture is not comprised of acetone, chloroform, and water in the proportions of 85:10:5, by volume;

(c) colorimetrically reacting the ethyl glucuronide on the chromatograph with a reagent comprising diphenylamine, aniline, and phosphoric acid, or DAP reagent; and (d) extracting the ethyl glucuronide from the chrornatograph with a water-containing organic solvent mixture;

(e) subjecting the extracted ethyl glucuronide to acid hydrolysis;

(f) subjecting the acid-hydrolyzed ethyl glucuronide to ascending chromatography on an absorbent substrate material using a solvent capable of resolving the acid hydrolyzed components; wherein the solvent components are not acetone, chloroform, and water in the proportions of 85; 10:5, by volume; and (g) isolating the separated components of the acid-hydrolyzed ethyl glucuronide from the chromatograph by scraping and eluting into water-containing organic solvent.

26. The method of claim 25, wherein the fluid sample of step (a) is a urine sample.

27. The method of claim 25, wherein the extracted ethyl glucuronide of step (e) is acid hydrolyzed in 1N hydrochloric acid (HCl) at about 80° C. for approximately 15 hours.

28. The method of claim 23 or claim 25, wherein the solvent mixture used in step (b) is comprised of chloroform, methanol, and water in the proportions of 65:35:5, by volume.

29. The method of claim 25; wherein the solvent mixture used in step (f) is comprised of cholorform, methanol, acetic acid, and water in the proportions of 50:20:6:1.5, by volume.

30. The method of claim 23 or claim 25, wherein the ethyl glucuronide of step (d) is extracted by scraping from the chromatograph and eluting with a solvent mixture comprising chloroform, methanol, and water in the proportions of 1:1:0.3, by volume.

31. A rapid and simple spot test method for diagnosing chronic alcoholism by detecting ethyl glucuronide, a biomarker whose presence in a fluid sample is specifically associated with chronic alcoholism, comprising the steps of:
 (a) obtaining a pre-determined volume of a sample from an individual being tested for the presence of ethyl glucuronide indicative of chronic alcohol consumption, wherein the sample is obtained at least 7 days after the individual has terminated alcohol consumption;
 (b) spotting the sample onto an absorbent substrate;
 (c) reacting the sample with a reagent comprising diphenylamine, aniline, and phosphoric acid or DAP reagent; and
 (d) observing if there is a colorimetric reaction in the localized area of the spot, with the colorimetric reaction indicating the presence of alcohol-specific ethyl glucuronide in the sample, wherein the presence of ethyl glucuronide is diagnostic of chronic alcoholism.

32. The method of claim 31, wherein in step (a), the sample is a urine sample.

33. The method of claim 32, wherein, in step (a) the urine sample is not concentrated.

34. The method of claim 31 or claim 32, further comprising: (g) assaying the test sample for the presence or absence of diabetes-associated glucose.

35. The method of claim 31, wherein in step (a) a pre-determined volume of a fluid sample from an individual who is a non-alcoholic and non-diabetic, and a pre-determined volume of a fluid sample containing ethyl glucuronide are provided as control samples, and further comprising the steps of:
 (e) spectrophotometrically measuring the amount of color observed in the localized spots of the test and control samples after step (c);
 (f) comparing the spectrophotometric measurements to determine if the test sample contains the ethyl glucuronide.

36. The method of claim 31 or claim 35, wherein steps (d), (e) and (f) are performed by an automatic analyzer and spectrophotometer connected therewith.

37. A method for diagnosing chronic alcoholism in an individual, comprising the steps of:
 (a) obtaining a pre-determined volume of a body fluid sample from the individual being tested for the presence of ethyl glucuronide, the ethyl glucuronide being a specific biomarker of chronic alcoholism, wherein the sample is obtained from an individual at least 7 days after termination of the consumption of alcohol by the individual and further wherein the ethyl glucuronide is detectable at least 7 days after the individual has terminated alcohol consumptuion;
 (b) subjecting the sample to ascending chromatography on an absorbent substrate using a water-containing organic solvent mixture capable of resolving the ethyl glucuronide from the substrate origin; wherein the solvent mixture is not comprised of acetone, chloroform, and water in the proportions of 85:10:5, by volume;
 (c) applying a reagent comprising diphenylamine, aniline, and phosphoric acid, or DAP reagent, to the chromatograph; and
 (d) observing the chromatograph to see if there is a colorimetric reaction at the position where the chromatographed ethyl glucuronide migrates, with the colorimetric reaction between the DAP reagent and the ethyl glucuronide indicating chronic alcoholism in the test individual.

38. The method of claim 37, wherein the sample of step (a) is a urine sample.

39. The method of claim 38, wherein the urine sample of step (a) is not concentrated.

40. The method of claim 37, wherein in step (a), a pre-determined volume of a negative control sample from a non-alcoholic, non-diabetic and a positive control sample containing ethyl glucuronide are provided.

41. The method of claim 40, further comprising:
 (e) spectrophotometrically measuring the amount of color of the chromatograph at the migration positions of the test and control samples after step (d);
 (f) comparing the results of the spectrophotometric measurement for the colorimetric reaction in the test sample with the spectrophotometric measurements for the calorimetric reaction in the positive control sample to quantify the presence of ethyl glucuronide; and optionally
 (g) assaying the test sample for the presence of diabetes-associated glucose.

42. A rapid and simple spot assay method for diagnosing chronic alcoholism, comprising the steps of:
 (a) obtaining a test sample from a person being tested for chronic alcoholism, wherein the sample is obtained from the person at least 7 days after termination of the consumption of alcohol by the person;
 (b) obtaining a negative control sample from a non-alcoholic and non-diabetic person and a positive control sample containing ethyl glucuronide, said ethyl glucuronide being a biomarker that diagnoses chronic alcoholism;
 (c) applying the samples as spots onto a thin layer chromatography plate coated with silica gel G;
 (d) drying the samples on the plate;
 (e) wettably contacting the dried plate and sample spots with a reagent comprising diphenylamine, aniline, and phosphoric acid or DAP reagent, wherein the DAP reagent can colorimetrically react with ethyl glucuronide in the control and test sample, if present in the test sample, and drying the plate; and
 (f) comparing the results of the colorimetric reactions in the control and test samples such that the absence of color in the negative control sample spot, the presence of color in the positive control sample spot, and the presence of color in the test sample spot identifies the test person as a chronic alcoholic.

43. The method of claim 42, wherein the test sample in step (a) is a urine sample.

44. The method of claim 43, wherein the urine test sample in step (a) is not concentrated.

45. The method according to claim 42, further comprising the step of:
(g) assaying the same or different sample from the test person for the presence of diabetes-associated glucose.

46. The assay method of any one of claims 1, 10, 31, 37, or 42, wherein the test sample is obtained from a pregnant woman for use in diagnosing fetal alcohol syndrome.

47. In a method of detecting ethyl glucuronide in a human sample, the improvement comprising a simple and rapid spot assay in which the presence of ethyl glucuronide in a sample aliquot diagnoses an individual as a chronic alcoholic, said method comprising:
(a) obtaining a pre-determined volume of the sample from an individual being tested for the presence of ethyl glucuronide that is indicative of chronic alcohol consumption, wherein the sample is obtained from the individual at least 7 days after termination of the consumption of alcohol by the individual;
(b) spotting the sample onto an absorbent substrate;
(c) reacting the sample with a reagent comprising diphenylamine, aniline, and phosphoric acid or DAP reagent; and
(d) observing if there is a colorimetric reaction in the localized area of the spot, with the colorimetric reaction indicating the presence of alcohol-specific ethyl glucuronide in the sample, thereby diagnosing the individual as a chronic alcoholic.

48. The method according to claim 47, wherein in step (a), the sample is a urine sample.

49. The method according to claim 48, wherein, in step (a) the urine sample is not concentrated.

50. The method according to claim 47 or claim 48, further comprising:
(g) assaying the test sample for the presence or absence of diabetes-associated glucose.

51. The method according to claim 47, wherein in step (a) a pre-determined volume of a fluid sample from an individual who is a non-alcoholic and non-diabetic, and a pre-determined volume of a fluid sample containing ethyl glucuronide are provided as control samples, and further comprising the steps of:
(e) spectrophotometrically measuring the amount of color observed in the localized spots of the test and control samples after step (d);
(f) comparing the spectrophotometric measurements to determine if the test sample contains the ethyl glucuronide.

52. The method according to claim 47 or claim 51, wherein steps (b), (e), and (f) are performed by an automatic analyzer and a spectrophotometer connected therewith.

53. In a method of detecting ethyl glucuronide in a human sample, the improvement comprising an ascending chromatography assay in which the localization and resolution of ethyl glucuronide in a sample aliquot diagnoses an individual as a chronic alcoholic, said method comprising the steps of:
(a) obtaining a pre-determined volume of a body fluid sample from the individual being tested for the presence of ethyl glucuronide, said ethyl glucuronide being a specific biomarker of chronic alcoholism; wherein the sample is obtained from the individual at least 7 days after termination of alcohol consumption by the individual;
(b) subjecting the sample to ascending chromatography on an absorbent substrate using a water-containing organic solvent mixture capable of resolving the ethyl glucuronide and localizing the ethyl glucuronide at a position on the substrate away from the substrate origin; wherein the solvent mixture used to resolve the ethyl glucuronide is not comprised of acetone, chloroform, and water in the proportions of 85:10:5, by volume;
(c) applying a reagent comprising diphenylamine, aniline, and phosphoric acid, or DAP reagent, to the chromatograph; and
(d) observing the chromatograph to see if there is a colorimetric reaction at the position where the chromatographed ethyl glucuronide migrates, with the colorimetric reaction between the DAP reagent and the ethyl glucuronide indicating the presence of ethyl glucuronide in the test sample and reliably diagnosing the individual as a chronic alcoholic.

54. The method according to claim 53, wherein the sample of step (a) is a urine sample.

55. The method according to claim 54, wherein the urine sample of step (a) is not concentrated.

56. The method according to claim 53, wherein step (a), a pre-determined volume of a negative control sample from a non-alcoholic, non-diabetic and a positive control sample containing ethyl glucuronide are provided.

57. The method according to claim 56, further comprising:
(e) spectrophotometrically measuring the amount of color of the chromatograph at the migration positions of the test and control samples after step (d);
(f) comparing the results of the spectrophotometric measurement for the colorimetric reaction in the test sample with the spectrophotometric measurements for the colorimetric reaction in the positive control sample to quantify the presence of ethyl glucuronide; and optionally
(g) assaying the test sample for the presence of diabetes-associated glucose.

58. In a method of detecting ethyl glucuronide in a human body fluid sample, the improvement comprising a rapid assay method in which the detection of ethyl glucuronide in a sample aliquot diagnoses an individual as a chronic alcoholic, said method comprising the steps of:
(a) obtaining a control sample from a non-alcoholic and non-diabetic person;
(b) obtaining a test sample from a person being tested for chronic alcoholism; wherein the sample is obtained from the person at least 7 days after termination of the consumption of alcohol by the person;
(c) subjecting the control and test samples to ascending chromatography on absorbent substrate in a water-containing organic solvent mixture suitable for separating alcohol-specific ethyl glucuronide if present in the test sample, wherein the organic solvent mixture used to resolve the ethyl glucuronide is not comprised of acetone, chloroform, and water in the proportions of 85:10:5, by volume;
(d) adding a reagent comprising diphenylamine, aniline, and phosphoric acid, or DAP reagent to the chromatograph, with the DAP reagent colorimetrically reacting with the ethyl glucuronide if present in the sample; and
(e) comparing the results of the control and test samples such that the presence of color in the test sample indicates a reaction of the DAP reagent with ethyl glucuronide and identifies the test person as a chronic alcohol consumer.

59. The assay method according to claim 58, further comprising the step of testing a second sample from the test person to independently identify diabetes-associated glucose in the test person.

60. The assay method according to claim 59, wherein the body fluid samples to be assayed are selected from the group consisting of blood, serum, plasma, saliva, amniotic fluid, urine, and body tissue fluid preparation.

61. The assay method according to claim 60, wherein the fluid sample is urine.

62. The assay method according to claim 61, wherein the urine sample is not concentrated.

63. The assay method according to claim 58, claim 61, or claim 62, wherein the solvent mixture used in step (c) is comprised of chloroform, methanol, and water in the proportions of 65:35:5, by volume, or chloroform, methanol, acetic acid, and water in the proportions of 50:20:6:1.5, by volume.

64. The assay method according to claim 63, further comprising the step of quantitatively determining the amount of the DAP reagent reactive with said samples of step (d) on the chromatograph substrate using spectrophotometric densitometry analysis.

65. The assay method of claim 58, wherein the test sample is an unconcentrated urine sample; wherein a small amount of the urine is spotted onto the chromatography plate and the spotted chromatography plate is dried; wherein the chromatography plate is developed in a solvent mixture comprised of chloroform, methanol, and water in the proportions of 65:35:5, by volume, or in a solvent mixture comprising chloroform, methanol, acetic acid, and water in the proportions of 50:20:6:1.5, by volume, until the solvent front has moved a suitable distance away from the sample spot, and the developed chromatography plate is dried; and wherein DAP reagent is applied to the developed chromatography plate and the chromatography plate is dried.

66. A simple, reliable, and sensitive high pressure liquid chromatographic method of diagnosing chronic alcoholism in an individual by detecting ethyl β-glucuronide in a body fluid sample from the individual, said ethyl glucuronide being diagnostic of chronic alcoholism, comprising:

(a) obtaining an aliquot of said sample from the individual being tested for chronic alcoholism, said sample being obtained at least 7 days after termination of alcohol consumption by the individual;

(b) derivatizing said sample aliquot;

(c) subjecting said derivatized sample of step (b) to high pressure liquid chromatography to generate a high pressure liquid chromatography chromatography; and (d) observing a peak on said chromatograph of step (c) having a retention time coincident with that of derivatized ethyl β-glucuronide, wherein the presence of said ethyl glucuronide peak is a diagnostic biomarker of chronic alcoholism.

67. The method according to claim 66, wherein in step (a), the sample is a urine sample.

68. The method according to claim 67, wherein, in step (a) the urine sample is not concentrated.

69. The method according to claim 68, wherein said sample aliquot of step (a) is about 5 μL.

70. The assay method according to claim 66, wherein the body fluid sample to be tested is selected from the group consisting of blood, serum, plasma, saliva, amniotic fluid, and body tissue fluid preparation.

71. The method of claim 66, wherein said derivatizing step (b) results in a phenylacyl derivative of said sample aliquot.

* * * * *